US012644888B2

(12) United States Patent
Lim et al.

(10) Patent No.: US 12,644,888 B2
(45) Date of Patent: Jun. 2, 2026

(54) METHODS FOR TREATING CEREBRAL VASOSPASM WITH A PD-1 AGONIST

(71) Applicant: THE JOHNS HOPKINS UNIVERSITY, Baltimore, MD (US)

(72) Inventors: Michael Lim, Reisterstown, MD (US); Christopher Jackson, Baltimore, MD (US); Rafael J. Tamargo, Baltimore, MD (US); John Choi, Palo Alto, CA (US)

(73) Assignee: The Johns Hopkins University, Baltimore, MD (US)

( * ) Notice: Subject to any disclaimer, the term of this patent is extended or adjusted under 35 U.S.C. 154(b) by 1088 days.

(21) Appl. No.: 17/626,679

(22) PCT Filed: Jul. 13, 2020

(86) PCT No.: PCT/US2020/041769
§ 371 (c)(1),
(2) Date: Jan. 12, 2022

(87) PCT Pub. No.: WO2021/011448
PCT Pub. Date: Jan. 21, 2021

(65) Prior Publication Data
US 2022/0252599 A1      Aug. 11, 2022

Related U.S. Application Data

(60) Provisional application No. 62/873,439, filed on Jul. 12, 2019.

(51) Int. Cl.
| *A61P 9/10* | (2006.01) |
| *A61K 38/17* | (2006.01) |
| *A61K 39/395* | (2006.01) |
| *C07K 14/705* | (2006.01) |
| *G01N 33/569* | (2006.01) |
| *A61K 39/00* | (2006.01) |

(52) U.S. Cl.
CPC ... *G01N 33/56972* (2013.01); *A61K 38/1774* (2013.01); *A61K 39/3955* (2013.01); *A61P 9/10* (2018.01); *C07K 14/70532* (2013.01); *A61K 2039/505* (2013.01); *C07K 2319/00* (2013.01); *G01N 2333/70532* (2013.01); *G01N 2800/2871* (2013.01); *G01N 2800/52* (2013.01)

(58) Field of Classification Search
CPC . C07K 14/70532; A61K 38/1774; A61P 9/10; G01N 2333/70532; G01N 33/56972
See application file for complete search history.

(56) References Cited

U.S. PATENT DOCUMENTS

| 4,103,687 A | 8/1978 | Ishii |
| 6,004,986 A | 12/1999 | Arthur et al. |
| 7,867,491 B2 | 1/2011 | Yang et al. |
| 8,586,038 B2 | 11/2013 | Yang et al. |
| 8,927,697 B2 | 1/2015 | Davis et al. |
| 9,181,342 B2 | 11/2015 | Davis |
| 9,683,043 B2 | 6/2017 | Davis et al. |
| 9,701,749 B2 | 7/2017 | Shibayama et al. |
| 2008/0305147 A1 | 12/2008 | Macdonald et al. |
| 2010/0042193 A1 | 2/2010 | Slavin |
| 2011/0171215 A1* | 7/2011 | Davis ........................ A61P 1/04 424/139.1 |
| 2012/0269806 A1* | 10/2012 | Sykes ....................... A61P 1/16 424/278.1 |

FOREIGN PATENT DOCUMENTS

| WO | 2002064022 | 8/2002 |
| WO | 2006127587 | 11/2006 |

OTHER PUBLICATIONS

Han et al., PD-L1 (Programmed Death Ligand 1) Protects Against Experimental Intracerebral Hemorrhage-Induced Brain Injury, Stroke, vol. 48, No. 8, pp. 2255-2262 (2017).

Han, R., et al. PD-L1 (Programmed Death Ligand 1) Protects Against Experimental Intracerebral Hemorrhage-Induced Brain Injury. Stroke. vol. 48, No. 8, Aug. 1, 2017, pp. 2255-2262.

Ren, X. Programmed Death-1 Pathway Limits Central Nervous System Inflammation and Neurologic Deficits in Murine Experimental Stroke. Stroke. vol. 41. No. 9, Sep. 1, 2011, pp. 2578-2583.

Chen, et al., Enhanced Expression of PD-L1 on Microglia after Surgical Brain Injury Exerts Self-Protection from Inflammation and Promotes Neurological Repair. Neurochemical Research (2019) 44: 2470-2481.

Wang, et al., PDL1 Fusion Protein Protects Against Experimental Cerebral Malaria via Repressing Over-Reactive CD8+ T Cell Responses. Frontiers in Immunology (2018) 9:3157, pp. 1-13.

Zhang, et al., Association Between Programmed Cell Death-1 and CD4+ T Cell Alternations in Different Phases of Ischemic Stroke Patients (2018) 12: 170, pp. 1-11.

Jedrzejowska-Szypulka,H. et al., "Neutralization of interleukin-1beta reduces vasospasm and alters cerebral blood vessel density following experimental subarachnoid hemorrhage in rats," Curr. Neurovasc Res., 6(2):95-103 (2009).

Yuan et al., "Programmed death (PD)-1 attenuates macrophage activation and brain inflammation via regulation of fibrinogen-like protein 2 (Fgl-2) after intracerebral hemorrhage in mice," Immunol. Lett., 179: 114-121 (2016).

Ferro, et al., Update on subarachnoid haemorrhage. J Neurol 255, 465-479 (2008).

(Continued)

*Primary Examiner* — Zachary C Howard
(74) *Attorney, Agent, or Firm* — Ballard Spahr LLP

(57)      ABSTRACT

The present invention relates to the field of inflammation. More specifically, the present invention provides compositions and methods for treating cerebral inflammation and associated sequelae thereof including cerebral vasospasm. In one embodiment, a method for treating cerebral vasospasm in a patient comprises the step of administering to the patient a PD-1 agonist, wherein a blood sample obtained from the patient comprises elevated PD-1 expression on monocytes relative to a control.

16 Claims, 23 Drawing Sheets

Specification includes a Sequence Listing.

(56)                    References Cited

OTHER PUBLICATIONS

Charpentier, et al., Multivariate analysis of predictors of cerebral vasospasm occurrence after aneurysmal subarachnoid hemorrhage. Stroke 130, 1402-8 (1999).

Hijdra, et al., Prediction of delayed cerebral ischemia, rebleeding, and outcome after aneurysmal subarachnoid hemorrhage. Stroke 19, 1250-6 (1988).

Chaichana, et al., Haptoglobin 2-2 Genotype Determines Chronic Vasospasm After Experimental Subarachnoid Hemorrhage. Stroke 38, 3266-3271 (2007).

Barber, et al., Restoring function in exhausted CD8 T cells during chronic viral infection. Nature 439, 682-687 (2005).

Fife, et al., The role of the PD-1 pathway in autoimmunity and peripheral tolerance. Annals of the New York Academy of Sciences 1217, 45-59 (2011).

Dong, et al., Tumor-associated B7-H1 promotes T-cell apoptosis: A potential mechanism of immune evasion. Nat Med 8, 793-800 (2002).

Topalian, et al., Immune Checkpoint Blockade: A Common Denominator Approach to Cancer Therapy. Cancer Cell 27, 450-461 (2015).

Gaetani, et al., Cisternal CSF levels of cytokines after subarachnoid hemorrhage. Taylor & Francis 20, 337-342 (2016).

Kaynar, et al., Detection of soluble intercellular adhesion molecule-1 and vascular cell adhesion molecule-1 in both cerebrospinal fluid and serum of patients after aneurysmal subarachnoid hemorrhage. Journal of Neurosurgery 101, 1030-1036 (2019).

Polin, et al., Detection of soluble E-selectin, ICAM-1, VCAM-1, and L selectin in the cerebrospinal fluid of patients after subarachnoid hemorrhage. Journal of Neurosurgery 89, 559-567 (2019).

Kikuchi, et al., Cytokine production in cerebrospinal fluid after subarachnoid haemorrhage. Taylor & Francis 17, 106-108 (2016).

Xie, et al., Increase ICAM-1 and LFA-1 expression by cerebrospinal fluid of subarachnoid hemorrhage patients: Involvement of TNF-alpha Brain Research 1512, 89-96 (2013).

Schneider, et al., Functional analysis of Pro-inflammatory properties within the cerebrospinal fluid after subarachnoid hemorrhage in vivo and in vitro. J Neuroinflammation 9, 330-2 (2012).

Barrow, et al., The role of inflammation and potential use of sex steroids in intracranial aneurysms and subarachnoid hemorrhage. Surg Neurol Int 9, 150-2 (2018).

Froehler, et al., Vasospasm after subarachnoid hemorrhage in haptoglobin 2-2 mice can be prevented with a glutathione peroxidase mimetic. Journal of Clinical Neuroscience 17, 1169-1172 (2010).

Schallner, et al., Microglia regulate blood clearance in subarachnoid hemorrhage by heme oxygenase-1. J. Clin. Invest. 125, 2609-2625 (2015).

Kubota, et al., The kinetics of lymphocyte subsets and macrophages in subarachnoid space after subarachnoid hemorrhage in rats. Am Heart Assoc 24, 1993-2000 (1993).

Provencio, et al., CSF Neutrophils Are Implicated in the Development of Vasospasm in Subarachnoid Hemorrhage. Neurocrit Care 12, 244-251 (2009).

Spitzer, et al., Activation of Cytotoxic Natural Killer Cells After Aneurysmal Subarachnoid Hemorrhage. World Neurosurgery 101, 666-676.e1 (2017).

Huang, et al., PD-1 expression by macrophages plays a pathologic role in altering microbial clearance and the innate inflammatory response to sepsis. Proceedings of the National Academy of Sciences 106, 6303-6308 (2009).

Loftus, et al., Beta-Blockade use for Traumatic Injuries and Immunomodulation. Shock 46, 341-351 (2016).

Bunc, et al., The influence of noradrenergic blockage on vasospasm and the quantity of cerebral dopamine ß-hydroxylase following subarachnoid haemorrhage in rabbits. Wien Klin Wochenschr 115, 652-659 (2003).

Chalouhi, et al., Beta-blocker therapy and impact on outcome after aneurysmal subarachnoid hemorrhage: a cohort study. Journal of Neurosurgery 125, 730-736 (2019).

Chang, et al., Beta Blockade and Clinical Outcomes in Aneurysmal Subarachnoid Hemorrhage. TONEUJ 10, 155-163 (2016).

Stansfield, et al., Clinical significance of monocyte heterogeneity. Clin Trans Med 4, 2527-2 (2015).

Mildner, et al., Genomic Characterization of Murine Monocytes Reveals C/EFPBeta Transcription Factor Dependence of Ly6C-cells. Immunity 46, 849-862.e7 (2017).

Prinz, et al., Tickets to the brain: Role of CCR2 and CX3CR1 in myeloid cell entry in the CNS. Journal of Neuroimmunology 224, 80-84 (2010).

Huo, et al., Role of vascular cell adhesion molecule-1 and fibronectin connecting segment-1 in monocyte rolling and adhesion on early atherosclerotic lesions. Circ Res 87, 153-159 (2000).

Yednock, et al., Prevention of experimental autoimmune encephalomyelitis by antibodies against alpha4beta1 integrin. Nature 356, 63-66 (1992).

De Rooij, et al., Incidence of subarachnoid haemorrhage: a systematic review with emphasis on region, age, gender and time trends. J Neurol Neurosurg Psychiatry, 78, 1365-1372 (2007).

Ingall, et al., A Multinational Comparison of Subarachnoid Hemorrhage Epidemiology in the Who Monica Stroke Study. Stroke, 31, 1054-1061 (2000).

Rincon, et al., The epidemiology of admissions of nontraumatic subarachnoid hemorrhage in the United States. Neurosurgery, 72, 217-22 (2013).

Dabus, et al., Current options for the management of aneurysmal subarachnoid hemorrhage-induced cerebral vasospasm: a comprehensive review of the literature. Interv Neurol, 2, 30-51 (2013).

Lynes, et al., Current Options and Future Directions in Immune Therapy for Glioblastoma. Front Oneal. 2018; 8:578; DOI: 10.3389/fonc.2018.00578.

Arrieta et al., Expression of PD-1/PD-LI and PD-L2 in peripheral T-cells from non-small cell lung cancer patients. Oncotarget. 2017; 8(60):101994-102005; DOI: 10.18632/oncotarget.22025.

Bodhankar, et al., PD-LI mAb Treats Ischemic Stroke by Controlling CNS Inflammation. Stroke. 2015; 46(10): 2926-; DOI: 10.1161/STROKEAHA.115.010592.

Yu, et al., Therapeutic Antibodies in Stroke. Transl. Stroke Res. 2013; 4:477-; DOI 10.1007 Is 12975-013-0281-2.

* cited by examiner

ICA PERFORATION MODEL (ICAp)  CISTERNA MAGNA INJECTION MODEL (CM)

MYELOID CELLS

CD4 T CELLS

CD8 T CELLS

GRANULOCYTES

NK CELLS

CHANGE IN % OF MONOCYTES PD-1+ vs. CHANGE IN TCD
VELOCITY THE FOLLOWING DAY r = 0.486 (95% CI 0.171 - 0.71)
p = 0.0037

CHANGE IN TCD MAX VELOCITY (cm/s)

CHANGE IN % OF MONOCYTES PD-1+

| PATIENT | CHANGE IN % OF MONOCYTES PD-1+ | CHANGE IN TCD VELOCITY THE FOLLOWING DAY |
|---|---|---|
| PATIENT 1 | -21.53 | 5 |
| | 1.96 | 22 |
| | 4.58 | 7 |
| | -1.77 | -2 |
| | 3.45 | -4 |
| | 4.23 | 23 |
| PATIENT 2 | 3.8 | 15 |
| | 0.88 | -2 |
| | -4.02 | 3 |
| | -1.98 | -2 |
| | 0.41 | -7 |
| | -2.78 | -2 |
| PATIENT 3 | 0.505 | 38 |
| | -0.25 | -10 |
| | 0.26 | 5 |
| | 1.62 | 3 |
| PATIENT 4 | 0.13 | -25 |
| | 1.27 | 20 |
| | -0.82 | -27 |
| | 2.95 | 5 |
| PATIENT 5 | 1.96 | 20 |
| | -1.22 | -10 |
| | 4.78 | 46 |
| | -4.53 | -32 |
| | 0.98 | 22 |
| | -0.18 | -4 |
| | 3.94 | -1 |
| PATIENT 6 | -0.93 | -3 |
| | -0.78 | -3 |
| | 2.82 | -3 |
| | 9.9 | 45 |
| | 0.5 | 65 |
| | -9.78 | -5 |
| | 2.28 | -3 |

Legend:

▨ PD1 < -5% OR VELOCITY < -10 cm/s

▨ PD1 -5 TO 0% OR VELOCITY -10 TO 0 cm/s

▨ PD1 0 TO 5% OR VELOCITY 0 TO 10 cm/s

▨ PD1 > 5% OR VELOCITY > 10 cm/s

STATS FOR RESULTS SECTION: %PD-1 CHANGE > 5% RESULTED IN AVERAGE TCD CHANGE OF 71.6% WHILE %PD-1 CHANGE <5% RESULTED IN AVERAGE % TCD CHANGE OF 24.0% (P = 0.003)

FIG. 3D

BRAIN MACROPHAGES

SEQUENCE LISTING

<160> NUMBER OF SEQ ID NOS: 1

<210> SEQ ID NO 1
<211> LENGTH: 290
<212> TYPE: PRT
<213> ORGANISM: Homo sapiens
<220> FEATURE:
<221> NAME/KEY: MISC_FEATURE
<222> LOCATION: (1)..(290)
<223> OTHER INFORMATION: PD-L1 amino acid sequence

<400> SEQUENCE: 1

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30
```

-continued

```
Gly Ser Asn Met Thr Ile Glu Cys Lys Phe Pro Val Glu Lys Gln Leu
        35              40              45

Asp Leu Ala Ala Leu Ile Val Tyr Trp Glu Met Glu Asp Lys Asn Ile
        50              55              60

Ile Gln Phe Val His Gly Glu Glu Asp Leu Lys Val Gln His Ser Ser
65              70              75              80

Tyr Arg Gln Arg Ala Arg Leu Leu Lys Asp Gln Leu Ser Leu Gly Asn
                85              90              95

Ala Ala Leu Gln Ile Thr Asp Val Lys Leu Gln Asp Ala Gly Val Tyr
                100             105             110

Arg Cys Met Ile Ser Tyr Gly Gly Ala Asp Tyr Lys Arg Ile Thr Val
            115             120             125

Lys Val Asn Ala Pro Tyr Asn Lys Ile Asn Gln Arg Ile Leu Val Val
        130             135             140

Asp Pro Val Thr Ser Glu His Glu Leu Thr Cys Gln Ala Glu Gly Tyr
145             150             155             160

Pro Lys Ala Glu Val Ile Trp Thr Ser Ser Asp His Gln Val Leu Ser
                165             170             175

Gly Lys Thr Thr Thr Thr Asn Ser Lys Arg Glu Glu Lys Leu Phe Asn
                180             185             190

Val Thr Ser Thr Leu Arg Ile Asn Thr Thr Thr Asn Glu Ile Phe Tyr
            195             200             205

Cys Thr Phe Arg Arg Leu Asp Pro Glu Glu Asn His Thr Ala Glu Leu
    210             215             220

Val Ile Pro Glu Leu Pro Leu Ala His Pro Pro Asn Glu Arg Thr His
225             230             235             240

Leu Val Ile Leu Gly Ala Ile Leu Leu Cys Leu Gly Val Ala Leu Thr
                245             250             255

Phe Ile Phe Arg Leu Arg Lys Gly Arg Met Met Asp Val Lys Lys Cys
                260             265             270

Gly Ile Gln Asp Thr Asn Ser Lys Lys Gln Ser Asp Thr His Leu Glu
        275             280             285

Glu Thr
290
```

METHODS FOR TREATING CEREBRAL VASOSPASM WITH A PD-1 AGONIST

CROSS-REFERENCE TO RELATED APPLICATIONS

This application is a 35 U.S.C. § 371 U.S. national entry of International Application PCT/US2020/041769, having an international filing date of Jul. 13, 2020, which claims the benefit of U.S. Provisional Application No. 62/873,439, filed Jul. 12, 2019, which is incorporated herein by reference in its entirety.

FIELD OF THE INVENTION

The present invention relates to the field of inflammation. More specifically, the present invention provides compositions and methods for treating cerebral inflammation and associated sequelae thereof including cerebral vasospasm.

INCORPORATION-BY-REFERENCE OF MATERIAL SUBMITTED ELECTRONICALLY

This application contains a sequence listing. It has been submitted electronically via EFS-Web as an ASCII text file entitled "P15683-02_ST25.txt." The sequence listing is 2,886 bytes in size, and was created on Jul. 8, 2020. It is hereby incorporated by reference in its entirety.

BACKGROUND OF THE INVENTION

Aneurysmal subarachnoid hemorrhage (aSAH) has an incidence of approximately 30,000 patients in the US annually. Cerebral vasospasm occurs 3-20 days after aneurysm rupture and is a significant source of morbidity and mortality for approximately 30% of patients with aSAH. Treatment of cerebral vasospasm currently consists of prophylactic nimodipine and supportive care with selective intra-arterial chemical and/or mechanical spasmolysis reserved for patients with refractory vasospasm resulting in acute ischemia. Aberrant inflammation has been implicated in cerebral vasospasm, although the precise mechanisms are poorly understood and there are currently no immunomodulatory agents used for vasospasm prophylaxis or treatment.

BRIEF DESCRIPTION OF THE FIGURES

FIG. 1A: ICA perforation (ICAp) and cisterna magna (CM) injection techniques. FIG. 1B: ICAp produces diffuse SAH. FIG. 1C-1D: CM injection results in minimal change in the caliber of the ipsilateral terminal ICA while ICAp results in severe vasospasm (p=0.0002). FIG. 1E: Flow cytometric analysis of brain myeloid cells (CD3−, CD45+, CD11b+), CD4 lymphocytes (CD3+, CD4+, CD8−), CD8 lymphocytes (CD3+, CD4−, CD8+), granulocytes (CD45+, CD11b+, Ly6 g+), and NK cells (CD45+, CD3−, CD49b+) showed an increase in PD-1 expression on myeloid cells in ICAp compared with CM (p=0.037). FIG. 1F: Administration of IP propranolol (5 mg/kg) one hour prior to ICAp decreased the frequency of PD-1+ brain myeloid cells at 24 hours (p=0.0009). Data were analyzed using a two-tailed T-test. Error bars represent+/−SEM.

FIG. 2A: Representative flow cytometry plots showing PD-1 expression on brain-infiltrating macrophages, microglia, peripheral blood monocytes, and bone marrow monocytes 6 hours, 24 hours, and 48 hours after ICAp. FIG. 2B: PD-1 expression is increased following ICAp on CD45-high brain macrophages (p=0.001) as well as monocytes in the blood (p=0.0063) and bone marrow (p=0.0059), but not on CD45-dim microglia. Data were analyzed using a two-tailed T-test. Error bars represent+/−SEM.

FIG. 3A-3E. PD-1+ monocyte frequency in the peripheral blood of aSAH patients correlates with changes in cerebral blood flow velocities the following day. FIG. 3A: Representative flow cytometry plots for Patient 5 days 1-8 after aneurysm rupture. In the CD 14 vs. CD16 plots red dots represent PD-1+ cells. FIG. 3B: Maximum TCD velocity and % PD-1+ monocytes over time. FIG. 3C: Linear regression analysis of change in % PD-1+ monocytes vs. change in maximum TCD velocity the following day excluding the day 3 timepoint outlier (>4× higher than the SD) from Patient 1. Correlation coefficient (r)=0.486 (95% CI 0.171-0.71) with p=0.0037. FIG. 3D: Heat map of % change in PD-1+ monocytes paired with % change in maximum TCD velocity the following day. FIG. 3E: Violin plots of maximum TCD values the following day for PD-1+ monocytes >5% vs. <5% (p=0.0012).

FIG. 4A: Representative H&E sections of the terminal segment of the ICA. FIG. 4B: IP injection of PD-L1 (50 g) 1 hour after ICAp prevents vasospasm at 48 hours (p<0.0001) while administration of 200 g PD-1 blocking antibodies 1 hour before ICAp abrogates the effect of PD-L1 on vasospasm (p<0.0001, ipsilateral; p=0.0002 contralateral). FIG. 4C-4D: PD-L1 administration increases the frequency of PD-1+, Ly6c+, CCR2+ monocytes in the blood at 48 hours. FIG. 4E-4F: SAH mice treated with PD-L1 have a higher frequency of VLA-4+ monocytes in the blood at 48 hours (p=0.032). FIG. 4G: The frequency of PD-1+, Ly6c+, CCR2+, CD45-high macrophages in the brain is lower in PD-L1 treated mice at 24 and 48 hours following ICAp. Data were analyzed using a two-tailed T-test. Error bars represent+/−SEM.

FIG. 6A: Representative histograms showing PD-1 expression on myeloid cells, CD4 T cells, CD8 T cells, granulocytes, and NK cells in CM and ICAp models. FIG. 6B: Mouse myeloid cell gating strategy.

3

4 mildly elevated and returned to levels not different from a healthy subject when vasospasm resolved.

Figure 12:
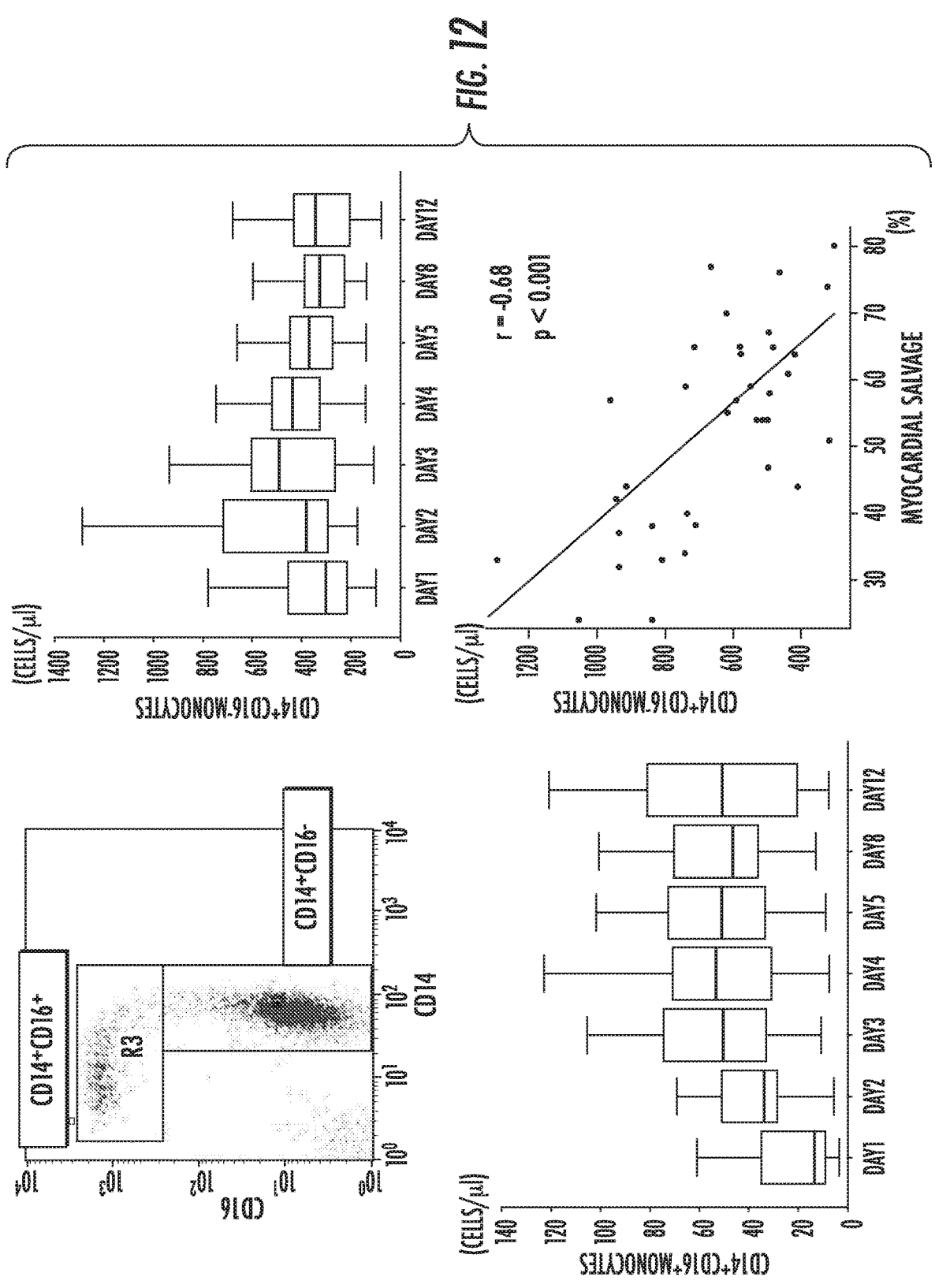

FIG. 12. The peak of CD14+, CD16– monocytes after myocardial infarction predicts myocardial salvage. The pattern observed in MI of an initial preponderance of CD14+, CD16– classical monocytes followed by an increase in CD16+ monocytes corresponds with the present inventors' data in subarachnoid hemorrhage. In addition, the present inventors have found that these cells express PD-1, which represents a novel therapeutic target for deactivating this pathologic cell population. Data above from Tsujioka et al.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The present invention is based, at least in part, on the discovery the PD-1 agonists can be used to treat cerebral inflammation and associated sequelae thereof including cerebral vasospasm. As described herein, the present inventors' data demonstrates that systemic administration of Programmed Death Ligand 1 (PD-L1) abrogates cerebral vasospasm in a murine model of subarachnoid hemorrhage by inhibiting PD-1 expressing myeloid cells. This pathway has not been previously described in cerebral vasospasm and represents a novel target for intervention.

By studying subarachnoid hemorrhage and vasospasm, the present inventors discovered that the PD-1/PD-L1 pathway is a novel mediator of inflammatory monocytes, which could be used to stop inflammation not only in vasospasm, but any disease cause by these cells. In particular embodiments, any disease known or found to be mediated by PD-1+, CD14+, CD6+ monocytes including, but not limited to myocardial infarction, stroke, kidney disease, inflammatory bowel disease and rheumatoid arthritis.

Accordingly, in one aspect, the present invention provides compositions and methods for detecting PD-1 expression. In certain embodiments, PD-1 expression on monocytes in a blood sample obtained from the patient is measured. PD-1 expression on monocytes can be measured using any available technique including, but not limited to, flow cytometry.

In other embodiments, a method comprises the step of administering a PD-1 agonist to a patient having an increased PD-1 expression on monocytes relative to a control. In certain embodiments, the PD-1 agonist is soluble PD-L1 or an analogue thereof. In a specific embodiment, soluble PD-L1 or an analogue thereof is a PD-L1 fusion protein. In a more specific embodiment, the PD-L1 fusion protein comprises GX-P2. In an alternative embodiment, the PD-1 agonist is an antibody or antigen-binding fragment thereof. In a more specific embodiment, the antibody or antigen-binding fragment thereof comprises CC-90006.

The present invention can be used to identify and/or monitor a patient having or suspected of having a condition associated with inflammatory monocytes expressing PD-1. In one embodiment, the patient suffers from an aneurysmal subarachnoid hemorrhage. Alternatively, the patient has cerebral vasospasm. In another embodiment, the patient has suffered a brain injury. In certain embodiments, the patient has suffered a hemorrhagic or ischemic stroke. In another embodiment, the patient has or suspected of having pathogenic monocyte-mediated inflammation. In such embodiments, the patient has a non-central nervous system condition or disease. In another specific embodiment, the patient has or is suspected of having monocyte-mediated cerebral inflammation.

In a further embodiment, the present invention provides a method for treating cerebral vasospasm in a patient comprising the step of administering to the patient a PD-1 agonist, wherein a blood sample obtained from the patient comprises elevated PD-1 expression on monocytes relative to a control. In another embodiment, a method for treating cerebral vasospasm in a patient comprises the steps of (a) measuring programmed death-1 (PD-1) expression on monocytes in a blood sample obtained from a patient; and (b) treating the patient with a PD-1 agonist if PD-1 expression is increased relative to a control. In a specific embodiment, the patient has suffered a brain injury. In another specific embodiment, the patient has suffered a stroke. In yet another embodiment, the patient has suffered a myocardial infarction.

In particular embodiments, the PD-1 agonist is soluble PD-L1 or a fragment or analogue thereof. The amino acid sequence of human PD-L1 is publicly available, Accession No. Q9NZQ7. See also SEQ ID NO:1.

In certain embodiments, the PD-1 agonist comprises an antibody or antigen-binding fragment thereof. In one embodiment, the PD-1 agonist antibody comprises CC-90006 (AnaptysBio, Inc. (San Diego, CA)). See, e.g., claims 1-139 of U.S. Pat. No. 10,428,145, which is incorporated by reference in its entirety. In another embodiment, the PD-1 agonist antibody comprises ANB030. In other embodiments, the PD-1 agonist is an antibody described in U.S. Pat. No. 9,181,342 (claims 1-14) and U.S. Pat. No. 8,927,697 (claims 1-10) (Isis Innovation Limited (Oxford, GB)), as well as U.S. Pat. No. 9,683,043 (claims 1-11) (Oxford University Innovation Limited (Oxford, GB)). In a further embodiment, the PD-1 agonist is an antibody described in U.S. Pat. No. 9,701,749 (claims 1-19) (Ono Pharmaceutical Co., Ltd. (Osaka, JP)). In yet another embodiment, the PD-1 agonist is an antibody described in U.S. Pat. No. 10,493,148 (claims 1-8) (Eli Lilly & Co. (Indianapolis, IN)). Further examples of PD-1 agonists that can be used in the present embodiments include, but are not limited to, UCB clone 19 or clone 10, PD1AB-1, PD1AB-2, PD1AB-3, PD1AB-4 and PD1AB-5, PD1AB-6 (Anaptys/Celgene), PD1-17, PD1-28, PD1-33 and PD1-35 (Collins et. al, US 2008/0311117A1 Antibodies against PD-1 and uses therefor, which is incorporated by reference).

In other embodiments, the PD-1 agonist is a fusion protein comprising PD-L1 or a fragment thereof. In a specific embodiment, the PD-1 agonist is GX-P2 (Genexine, Inc. (New York, NY)). See, e.g., U.S. Pat. No. 8,586,038 (claims 1-12) and U.S. Pat. No. 7,867,491 (claims 1-21).

In particular embodiments, the present invention provides compositions and methods directed to PD-1 signaling on monocytes/macrophages, rather than lymphocytes, where PD-1 has been much more extensively studied in the context of cancer immunotherapy. In PD-1 signaling on monocytes/ macrophages, at a minimum, there is no MHC/TCR inter-action, which is important for PD-1 signaling in lympho-cytes. Without being limited by any particular theory, the present inventors believe this is why soluble PD-L1 works in the model described herein (and potentially other diseases like MI and stroke), but has shown little effect in inhibiting lymphocytes. In fact, it is possible that specifically inhibiting monocytes could lead to less overall immunosuppression and lower the risk of infection. Thus, in certain embodi-ments, a PD-1 agonist is a monospecific PD-1 agonist such as soluble PD-L1 monomer.

In another aspect, the present invention provides diagnos-tic compositions and methods. As described further below, the present inventors have discovered that PD-1 expression on monocytes in the peripheral blood is elevated in patients with aneurysmal subarachnoid hemorrhage (aSAH) com-pared with normal controls. Importantly, cerebral vasospasm is preceded by a roughly 10-fold increase in the percent of monocytes expressing PD-1. Thus, in certain embodiments, PD-1 expression on monocytes can be used as a biomarker of pathologic brain inflammation in aneurysmal subarach-noid hemorrhage, hemorrhagic and ischemic stroke, as well as traumatic brain injury.

In another aspect, the present invention is directed to methods of screening for PD-1 agonists. In particular embodiments, the methods are directed to assessing how candidate agents act on different immune cell populations. In a specific embodiment, a method comprises culturing vari-ous immune cell lineages in vitro with candidate agonists and measuring function and/or cytokine secretion after stimulation. In an alternative embodiment, an in vivo screen is conducted with the ICAp SAH model described herein along with an infection model to identify candidates that prevent vasospasm, but also minimize the increased suscep-tibility to infection. In particular embodiments, a method is directed to PD-1 agonists for pathogenic monocyte-medi-ated inflammation.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combina-tions of reaction conditions, e.g., component concentrations, desired solvents, solvent mixtures, temperatures, pressures and other reaction ranges and conditions that can be used to optimize the product purity and yield obtained from the described process. Only reasonable and routine experimen-tation will be required to optimize such process conditions.

Example 1: PD-1+ Monocytes Mediate Cerebral Vasospasm Following Subarachnoid Hemorrhage Summary: Aneurysmal subarachnoid hemorrhage (aSAH) accounts for 5% of strokes, but disproportionately contributes to stroke-related morbidity and mortality.[1] Fol-lowing aneurysm rupture, radiographic cerebral vasospasm is detected in 70% of patients and 20% develop delayed cerebral ischemia (DCI)[2] The frequency and severity of cerebral vasospasm correlates with hemorrhage volume[3] and has been linked to aberrant inflammation.[4] The precise mechanisms of the underlying inflammatory process, how-ever, are unknown. Here the present inventors show that Programmed Death-1-expressing (PD-1+) monocytes are mediators of cerebral vasospasm following aSAH. The present inventors found that inflammatory PD-1+, Ly6c+, CCR2+ monocytes were released from the bone marrow and entered the peripheral blood in a catecholamine-dependent manner in an animal model of cerebral vasospasm. PD-1+ monocytes were also detected in the peripheral blood of patients with aSAH and the frequency of these cells corre-lated with changes in cerebral blood flow velocities. Treat-ing mice with soluble Programmed Death Ligand-1 (PD-L1) one hour after SAH prevented cerebral vasospasm and inhibited ingress of inflammatory monocytes into the brain. The present inventors' results identify PD-1+ monocytes as mediators of cerebral vasospasm and suggest PD-1 agonism as a potential therapeutic strategy. The present inventors anticipate that the discovery of a pathogenic role for PD-1+ monocytes will not only lead to development of a blood-based biomarker for cerebral vasospasm and a novel target for intervention in aSAH patients, but more broadly serve as a foundation for studying the PD-1 pathway in inflammatory disease mediated by innate immune cells.

PD-1 is an inhibitory immune checkpoint that limits collateral damage in the setting of chronic infection[5] and protects against autoimmunity.[6] The discovery that tumors use PD-1 signaling to obviate immune elimination[7] has become a cornerstone of clinical oncology.[8] Far less is known about the role of PD-1 in acute inflammation. Several studies have linked cerebral vasospasm to aberrant inflam-mation following aneurysm rupture[9-14]; however, the details of the underlying immune response are unclear. The present inventors sought to determine if PD-1 plays a role in the inflammatory response underlying cerebral vasospasm.

Materials and Methods

Mice. Male C57BL/6J mice (6-8 weeks) (Jackson Labo-ratory) were housed in pathogen-free conditions under ani-mal protocols approved by the Johns Hopkins University Institutional Animal Care and Use Committee (IACUC). For all experiments, mice were anesthetized with ketamine (100 mg/kg)/xylaine (10 mg/kg) by IP injection.

Histology. For experiments in which the endpoint was ICA measurement, mice were deeply anesthetized and underwent transcardial perfusion with 10 mL PBS followed by 4% paraformaldehyde/PBS. Brains were removed with care to preserve the intracranial vasculature by transecting the vessels sharply at the skull base. Brains were fixed in PFA for a minimum of 24 hours prior to cryoprotection in 30% sucrose/PBS for 48 hours at 4 degrees Celsius. Brains were embedded in paraffin, cut into 10 μm sections and stained with hematoxalyn and eosin (H&E).

Cisterna magna injection model. Mice were anesthetized and positioned prone with the head slightly flexed. A midline incision was made, and the posterior neck muscles were mobilized to visualize the occipital crest and the atlanto-occipital membrane. Blood was obtained from a donor mouse by cardiac puncture. The atlanto-occipital membrane was punctured with a 32 g needle to drain cerebrospinal fluid. 60 μL of blood were then injected into the subarach-noid space through the atlanto-occipital membrane using a Hamilton syringe and a 32 g needle over a period of approximately 2 minutes. The incision was closed, and mice were placed on a heating pad to recover.

ICA perforation model. Mice were anesthetized and posi-tioned supine. A midline incision was made from the ster-num to the jaw and the subcutaneous fat pad was mobilized under an operating microscope under low magnification. The fat pad was retracted superiorly, and the sternocleido-mastoid was retracted laterally to expose the common carotid artery. Under high magnification the carotid artery common, internal, and external carotid arteries were dis-sected free of the surrounding tissue. Disection of the internal carotid artery proceeded superior to at least the level of the pterygopaletine artery (PPA). 5-0 nylon sutures were then used to occlude the internal and common carotid arteries. The external carotid artery was permanently ligated with a 5-0 silk suture. After visual confirmation that blood flow was occluded the external carotid was transected and blood was irrigated from the lumen with sterile PBS. A 5-0 nylon suture (filament) was cut at an angle to create a sharp end. This end was passed into the lumen of the external carotid artery and guided into the internal carotid artery past the carotid bifurcation. At this point the 5-0 suture occluding the internal carotid artery was removed and the filament was guided past the PPA through the skull base under direct visualization. The suture was advanced until resistance was met at the ICA termination. At this point the filament was advanced an additional 2-3 mm until the resistance was no longer felt, indicating that the filament and passed through the vessel wall and into the subarachnoid space. A 5-0 silk suture was then tied loosely around the external carotid artery stump with the filament still in place. The filament was withdrawn, the 5-0 silk was tightened, and the 5-0 nylon suture occluding the common carotid artery was removed to allow reperfusion of the vessel. The incision was closed with a simple running suture and the mice were placed on a heating pad to recover.

Vessel measurements. Sections containing the terminal ICA were identified based on anatomic landmarks (FIG. 1). Images were obtained using a Zeiss Axiocam (Zeiss) micro-scope at 20× magnification. The vessel wall thickness and luminal diameter were measured using ImageJ (NIH).

Tissue harvest and cell preparation. Mice were deeply anesthetized and 60 μL of blood were drawn using capillary tubes via retro-orbital puncture. Red blood cells were lysed using ACK lysis buffer (Thermo Fisher) and resuspended in PBS for staining. Bilateral femurs and tibias were removed and bone marrow was aspirated, red blood cells were lysed in ACK lysis buffer, and remaining cells were resuspended in PBS for staining. Brains were removed and the tissue was mechanically dissociated, strained through a 70 um filter, and centrifuged in a 30%/70% PERCOLL® (Sigma-Al-drich) gradient at 2200 rpm for 20 minutes without brakes. Brain immune cells were extracted at the interface and resuspended in PBS for staining.

Staining and flow cytometric analysis of murine myeloid cells. Myeloid cells were stained for CD3, CD45, CD11b, CD11c, Ly6c, Ly6 g, CCR2, PD-1, VLA-4, and CD49b using the following anti-mouse antibodies: PerCP-Cy5.5 CD3 (BD, Lot 551163), APC/Fire 750 CD45 (BioLegend Lot 103154), AF700 CD11b BioLegend (Lot 101222), FITC CD11c BioLegend (Lot 117306), BV650 Ly6 g BioLegend (Lot 127641), PE CCR2 BioLegend (Lot 150610), PE-Cy7 PD-1 eBioscience (Lot 25-9985-82), BV421 PD-1 BioLeg-end (Lot 109121), APC CD49d (VLA-4) BioLegend (Lot 103622), PE CD49b (Pan-NK) BioLegend (Lot 108908). Data were acquired using a FACSCelesta (BD) and analyzed using FlowJo (BD).

Human subjects. All studies were approved by the Johns Hopkins Institutional Review Board (IRB). Six consecutive patients presenting to the Johns Hopkins Hospital or Johns Hopkins Bayview Medical Center with SAH and one or more cerebral aneurysms confirmed by cerebral angiogra-phy were enrolled in the study. Peripheral blood was drawn from an indwelling radial arterial catheter or venipuncture serially for up to 14 days following aneurysm rupture, corresponding with the vasospasm risk period. An average of 11 timepoints were obtained per patient with a range of 8-12 timepoints. TCD was performed as part of standard-of-care by a professional TCD technician and acquisition or interpretation of these data was not altered for this study. Patients underwent vascular imaging by CT angiogram, MR angiogram, and/or catheter-based angiography as clinically indicated. No clinical tests were obtained specifically for the purposes of this study.

Flow cytometric analysis of human monocytes. Leuko-cytes were isolated from whole blood samples by FICOLL® (Sigma-Aldrich) density gradient centrifugation. Cells were washed and resuspended in PBS and stained for CD3, CD45, CD11b, CD19, CD15, CD14, CD16 with the following anti-human antibodies: FITC CD3 (Biolegend, Lot 300440), AF700 CD45 (Biolegend, Lot 304024), BV421 CD11b (Biolegend, Lot 301324), FITC CD19 (Biolegend, Lot 302206), FITC CD15 (ThermoFisher, Lot 11-0159-42), APC-H7 CD14 (Biolegend, Lot 325620), PE-Cy7 CD 16 (Biolegend, Lot 302016). Data were acquired using a FACS-Celesta (BD) and analyzed using FlowJo (BD).

PD-L1 and anti-PD-1 administration. PD-L1 protein with a poly-His tag (ACROBiosystems, Cat PD1-M5220) was reconstituted in sterile PBS and 50 g was administered by IP injection 1 hour and 24 hours after ICAp. For experiments involving PD-1 blockade, anti-PD-1 monoclonal antibodies (hamster anti-mouse PD-1 purified from cultures of G4 hybridoma) were administered at a dose of 200 g by IP injection one hour prior to ICAp.

Statistical Analysis. All replicates were biological repli-cates. For the mouse experiments data were analyzed using a 2-tailed Student's T-test using GraphPad Prism software. $p < 0.05$ was considered significant. Multiple measurements on PD-1+ monocyte frequency and TCD velocities were obtained per patient. Changes in PD-1+ monocyte frequency and maximum TCD velocities were calculated by subtract-ing the value for each day from the day prior. Pearson correlation coefficient and inter-rater agreement of Cohen's kappa coefficient were estimated using the SAS software (version 9.4; SAS Institute).

Results and Discussion

Figure 1A:
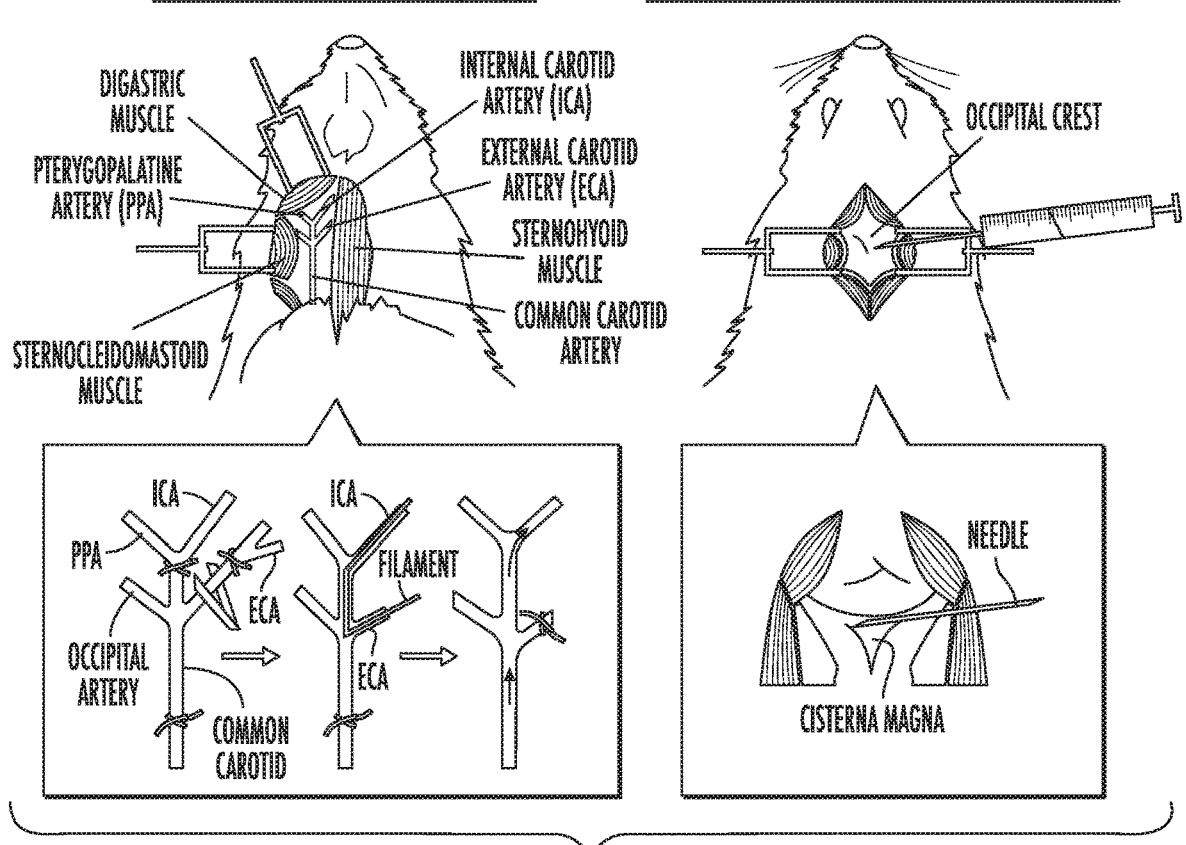
FIG. 1A-1F. Cerebral vasospasm is associated with an increased frequency of PD-1+ myeloid cells in the brain.
Figure 1B:
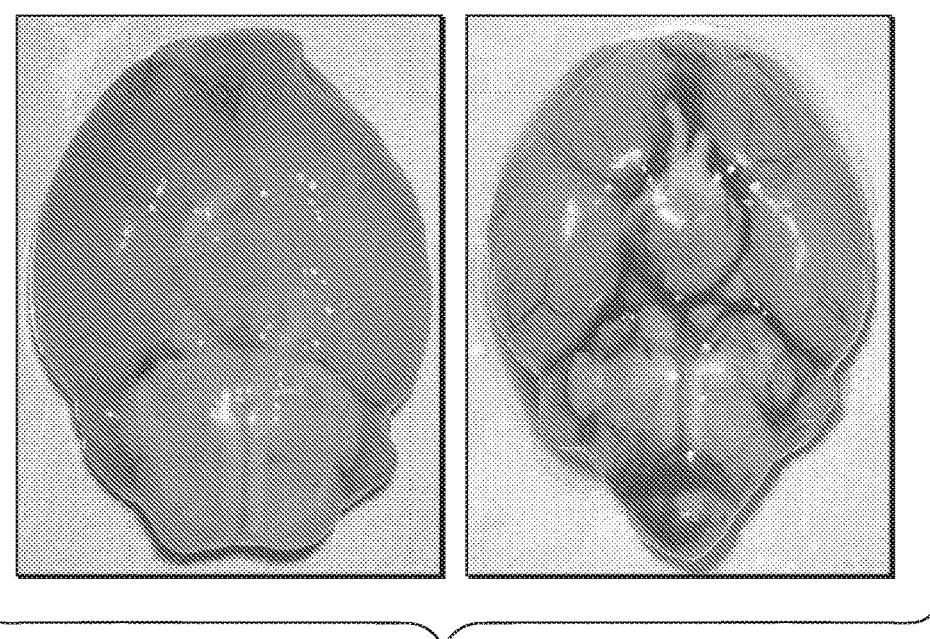
Figure 1C:
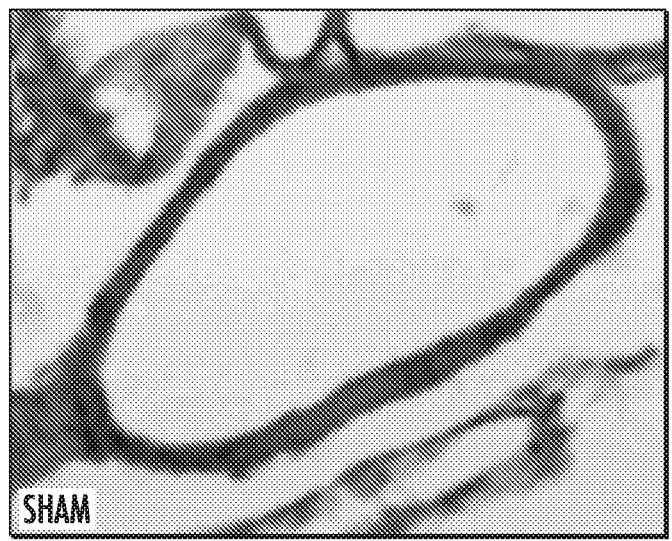
Figure 1C:
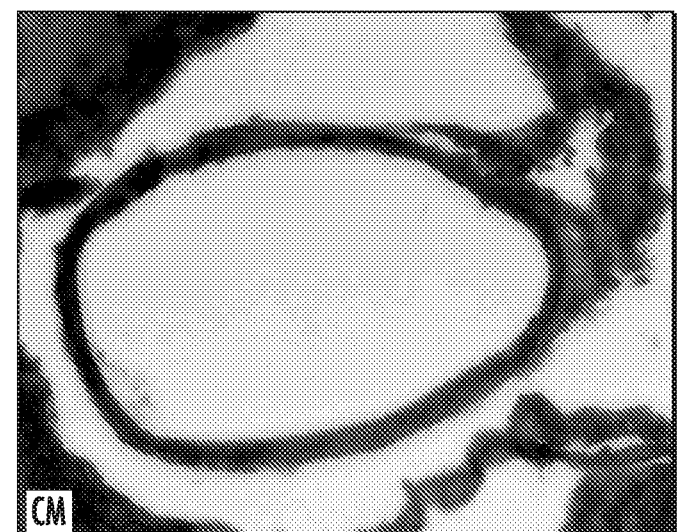
Figure 1C:
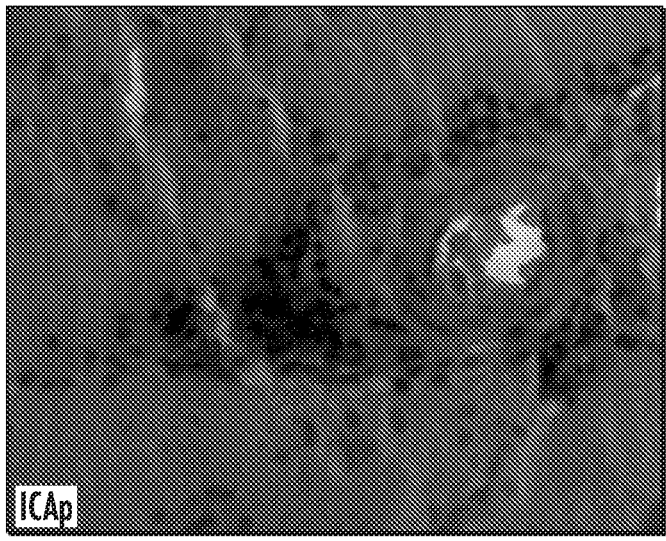
Figures 1D, 1E:
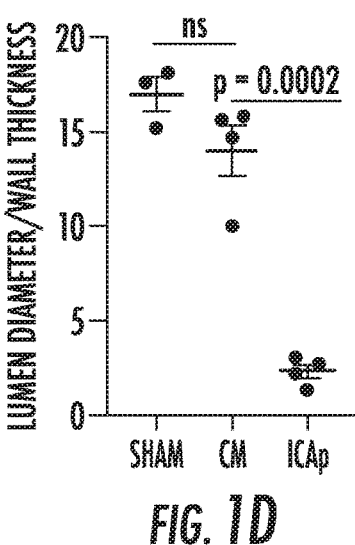
Figure 1F:
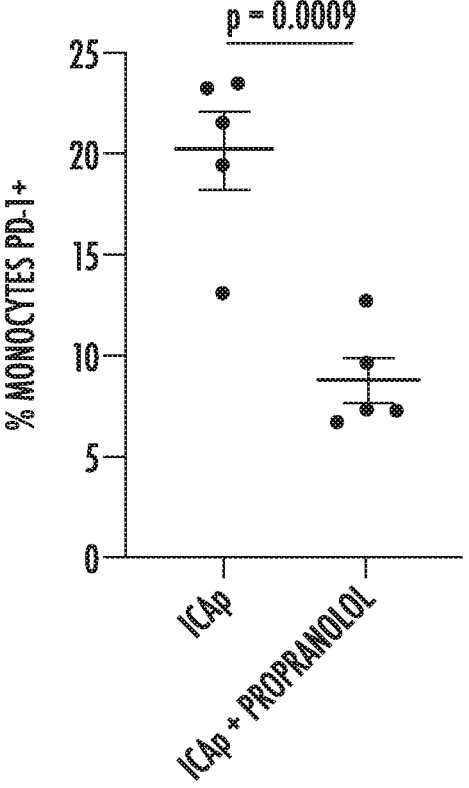
Figure 5:
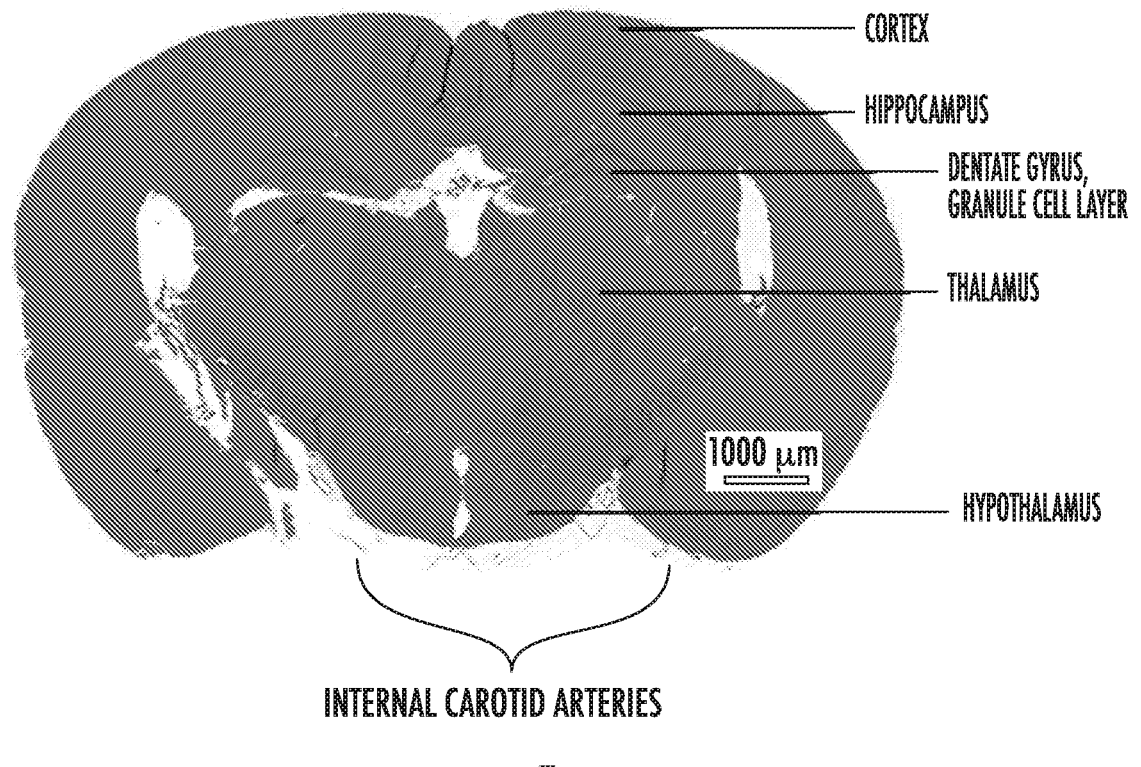
FIG. 5. Histologic localization of the terminal segment of the internal carotid arteries.

Critical illness and patient heterogeneity confound the inflammatory response in aSAH.[5] To identify specific mechanisms associated with cerebral vasospasm the present inventors compared two mouse models of SAH (FIG. 1A) by measuring the terminal segment of the internal carotid artery (ICA) (FIG. 5). Injecting blood into the cisterna magna (CM) causes vasospasm in pro-inflammatory hapto-globin 2-2 mice[4], but resulted in minimal vasospasm of the ICA in wild-type C57BL/6 mice (FIG. 1C,1D). Conversely, endovascular perforation of the ICA (ICAp) produced diffuse SAH (FIG. 1B) and severe vasospasm (FIG. 1C, 1D).

Figure 6A:
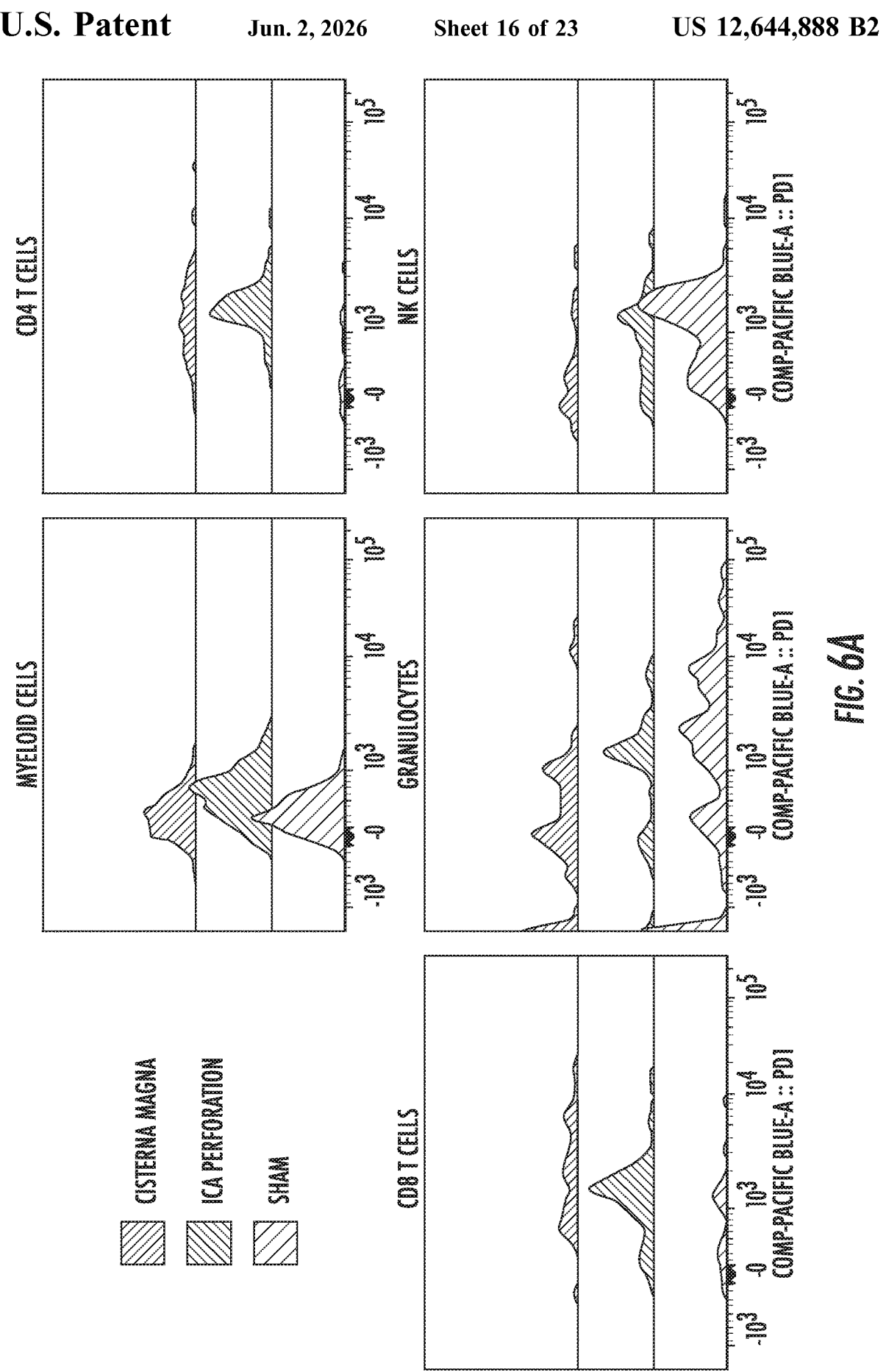
FIG. 6A-6B.
Figure 6B:
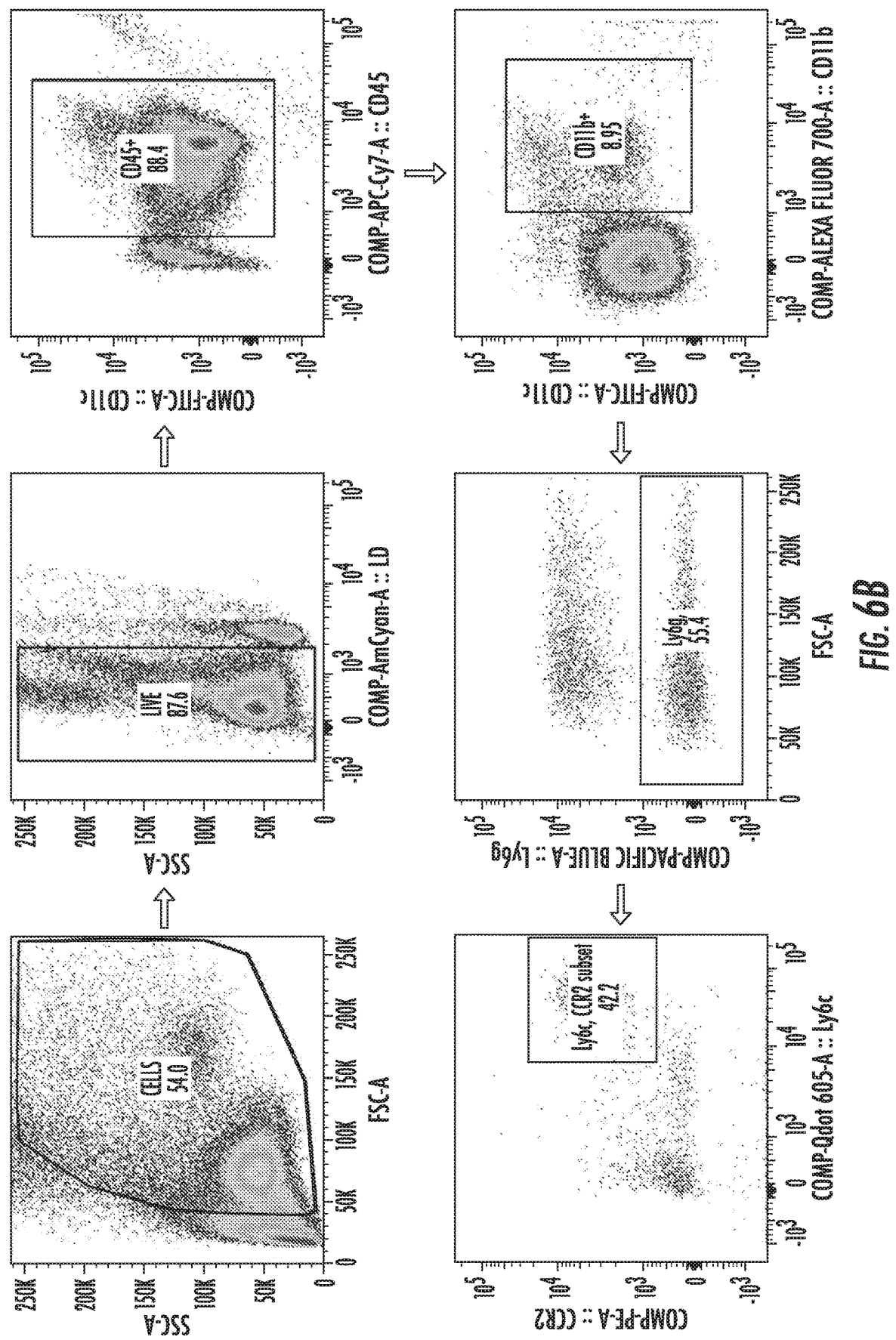

Diverse immune cell populations have been studied as mediators of cerebral vasospasm, including macrophages[16], microglia[17], lymphocytes[18], granulocytes[19], and natural killer (NK) cells[20]. The present inventors found that PD-1 expression varied among these brain-infiltrating immune cell populations (FIG. 6A). Only CD45+, CDIIb+ myeloid cells (FIG. S2b) exhibited a significant increase in PD-1 expression between the ICAp and CM models (FIG. 1E) (p=0.037). PD-1 inhibits macrophages in the setting of infection[21], but otherwise relatively little is known about the function of PD-1 signaling on myeloid cells. Based on the present inventors' data comparing the ICAp and CM models the present inventors hypothesized that PD-1+ macro-phages/microglia mediate the inflammatory response in cerebral vasospasm.

Figure 7:
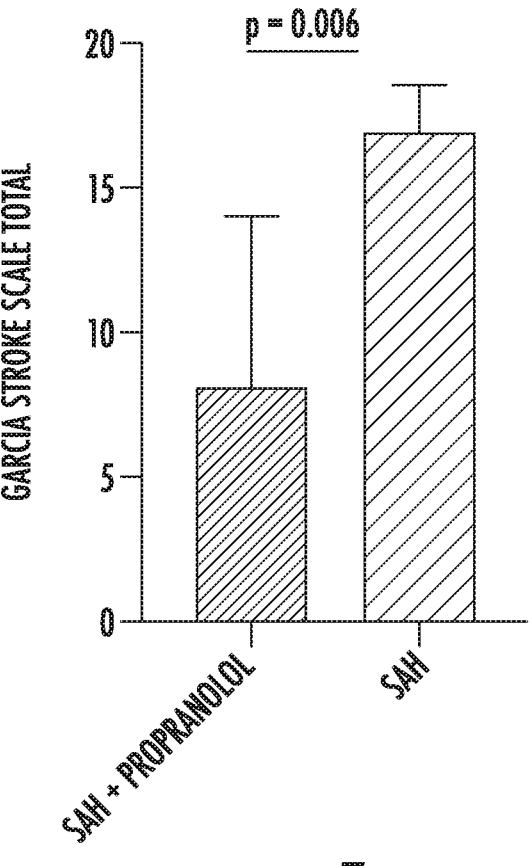
FIG. 7. Garcia stroke scale 48 hours after ICAp in mice with untreated SAH and SAH mice treated with propranolol.

To mechanistically link PD-1 expression on brain myeloid cells with SAH the present inventors tested the effects of beta-adrenergic blockade on the frequency of CD45+, CD11b+, PD-1+ brain myeloid cells following ICAp. Beta-adrenergic signaling stimulates a pro-inflammatory response in trauma and sepsis[22] and has been associated with cerebral vasospasm following aSAH.[23,24] The clinical effectiveness of beta blockade in aSAH, however, is equivocal[25]. Administering propranolol one hour prior to ICAp decreased the frequency of PD-1+ myeloid cells in the brain (FIG. 1F) (p=0.0009). Of note, these animals were sacrificed at 24 hours because the majority of propranolol-treated mice die prior to the 48-hour timepoint with severe neurologic deficits (FIG. 7). Taken together, these data suggest that the inconsistent clinical results of beta blockade in patients with aSAH may be due to competing effects of decreased local inflammation and impaired autoregulation of cerebral blood flow.

Figure 2A:
FIG. 2A-2B. PD-1+ monocytes are detectable in the bone marrow and peripheral blood following SAH.
Figure 2B:
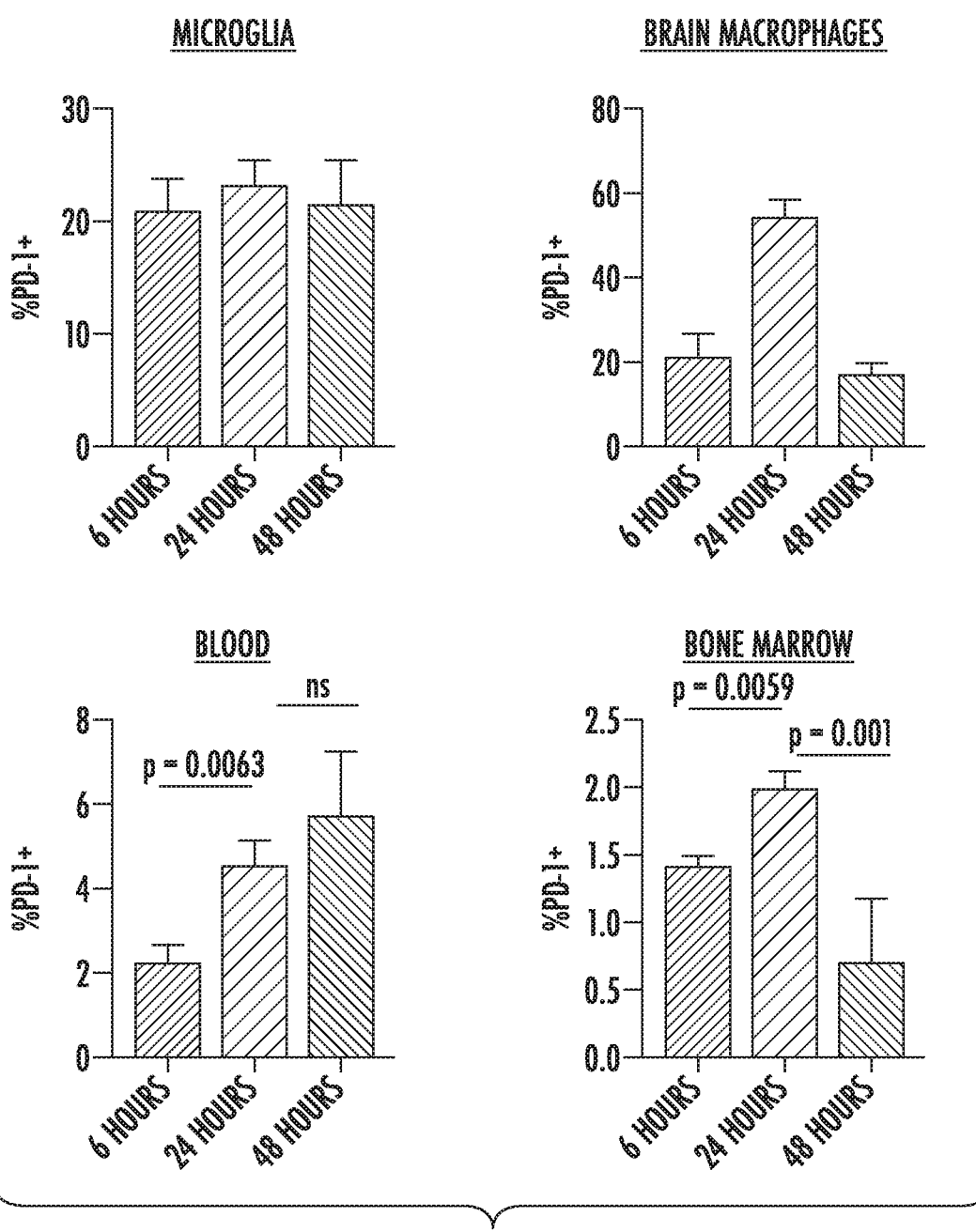

Involvement of the sympathetic nervous system sug-gested a systemic rather than local immune response. To determine the origin and timing of PD-1 expression on brain myeloid cells the present inventors harvested brains, periph-eral blood, and bone marrow from mice 6 hours, 24 hours, and 48 hours after ICAp. At the 6, 24, and 48-hour time-points CD45-dim microglia expressed stable levels of PD-1 (FIG. 2A). Conversely, the frequency of PD-1+ macro-phages increased from 6 to 24 hours (p=0.001) and returned to baseline at 48 hours (FIG. 2B). The pattern of PD-1 expression among peripheral monocytes corresponded with that of brain-infiltrating macrophages as the frequency of PD-1+ monocytes in the blood and bone marrow increased 24 hours after SAH (p=0.0063 and p=0.0059, respectively). These data demonstrate that SAH stimulates release of PD-1+ monocytes from the bone marrow and these mono-cytes subsequently traffic to brain in a time course concor-dant with cerebral vasospasm.

Figure 3A:
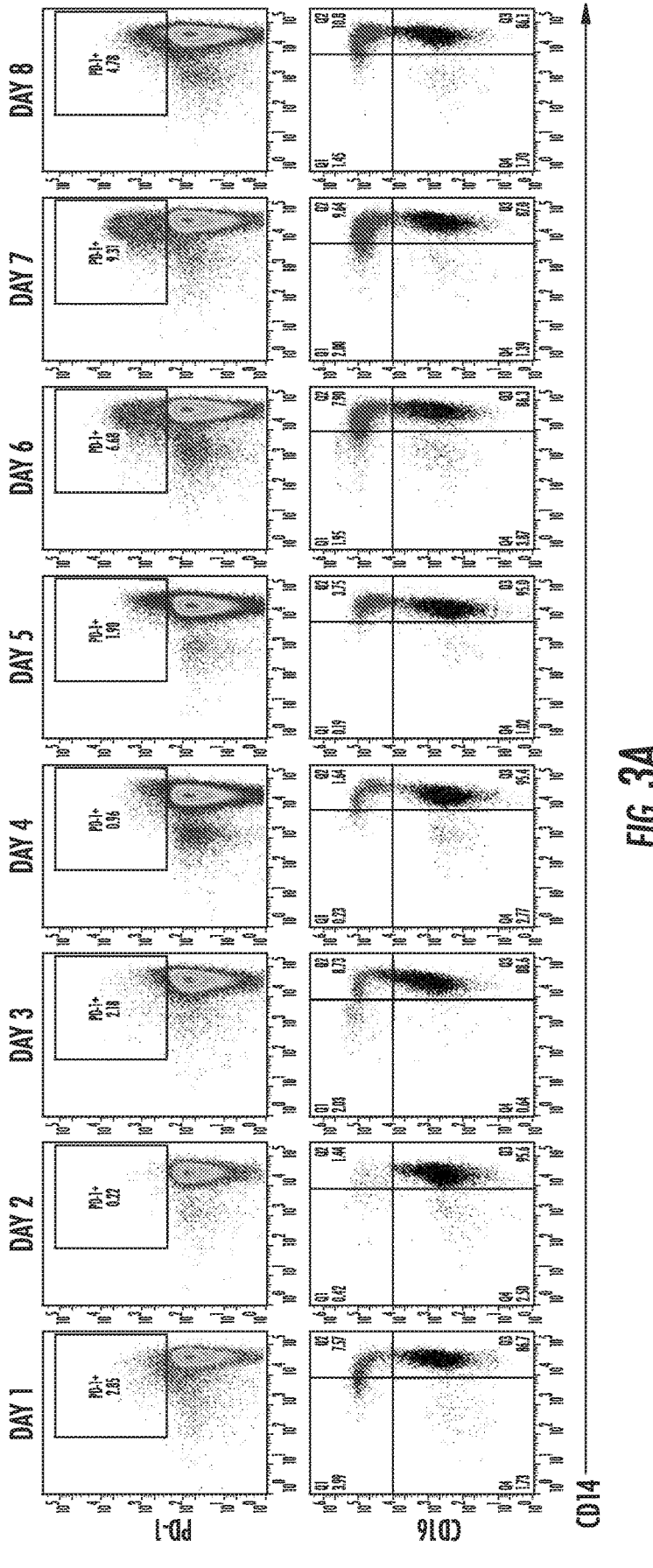
Figures 3B, 3C:
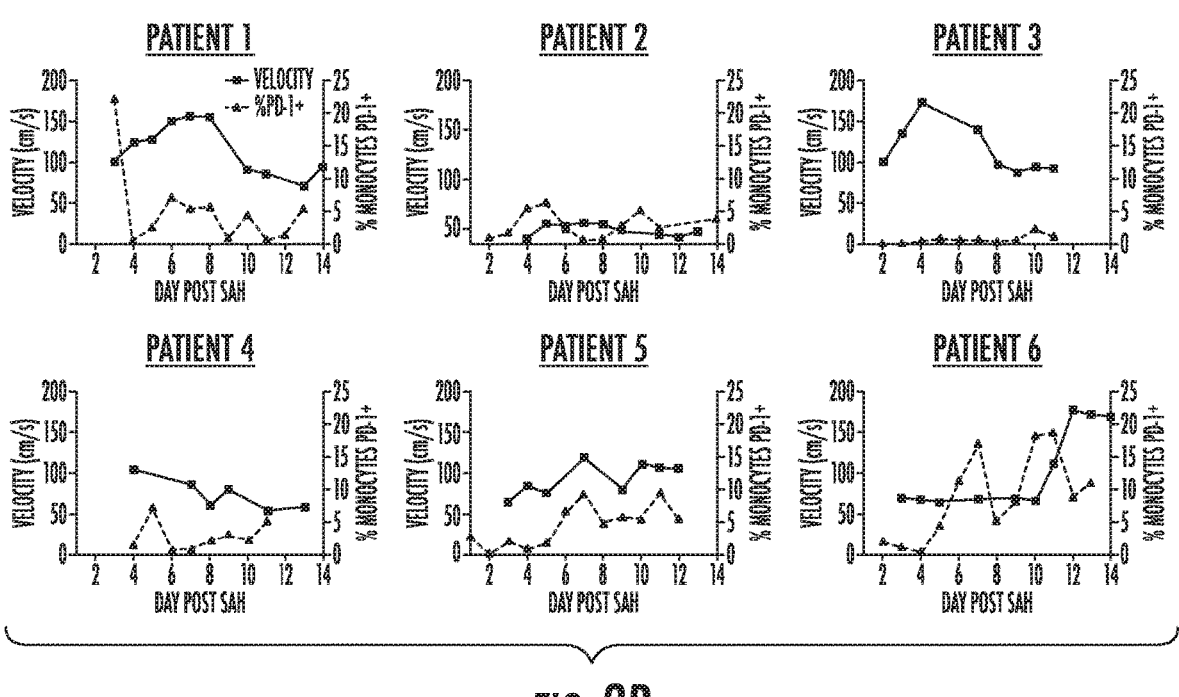
Figure 8:
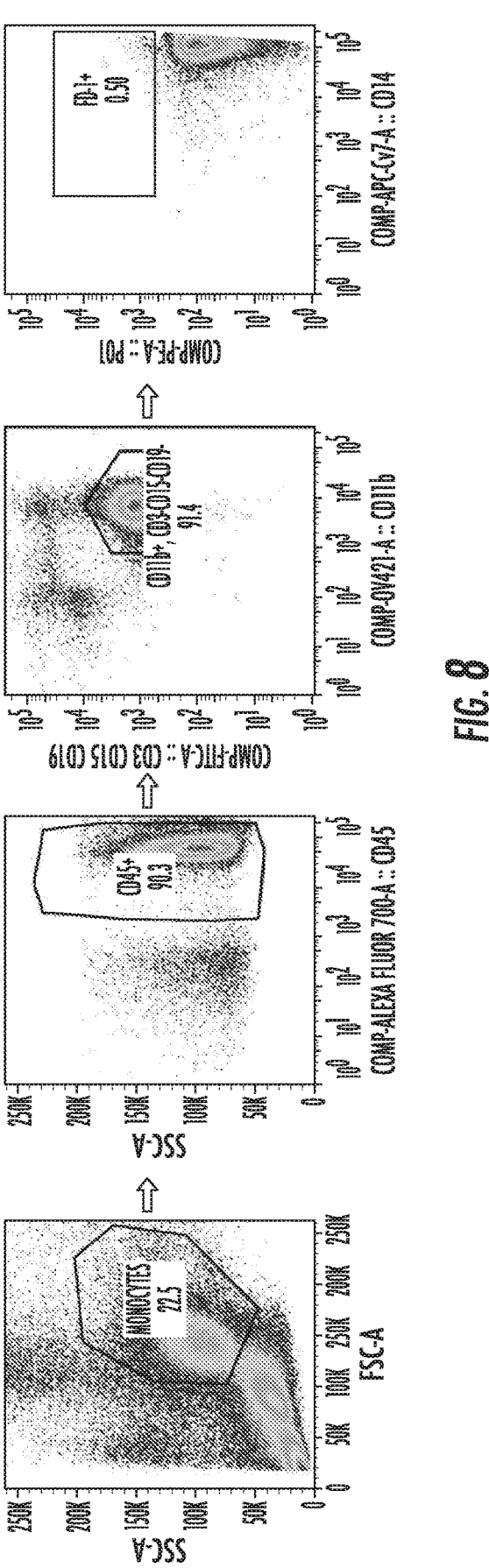
FIG. 8. Representative human myeloid cell gating strategy with PD-1 gates set for each patient based on fluorescence minus one (FMO) samples.
Figure 9:
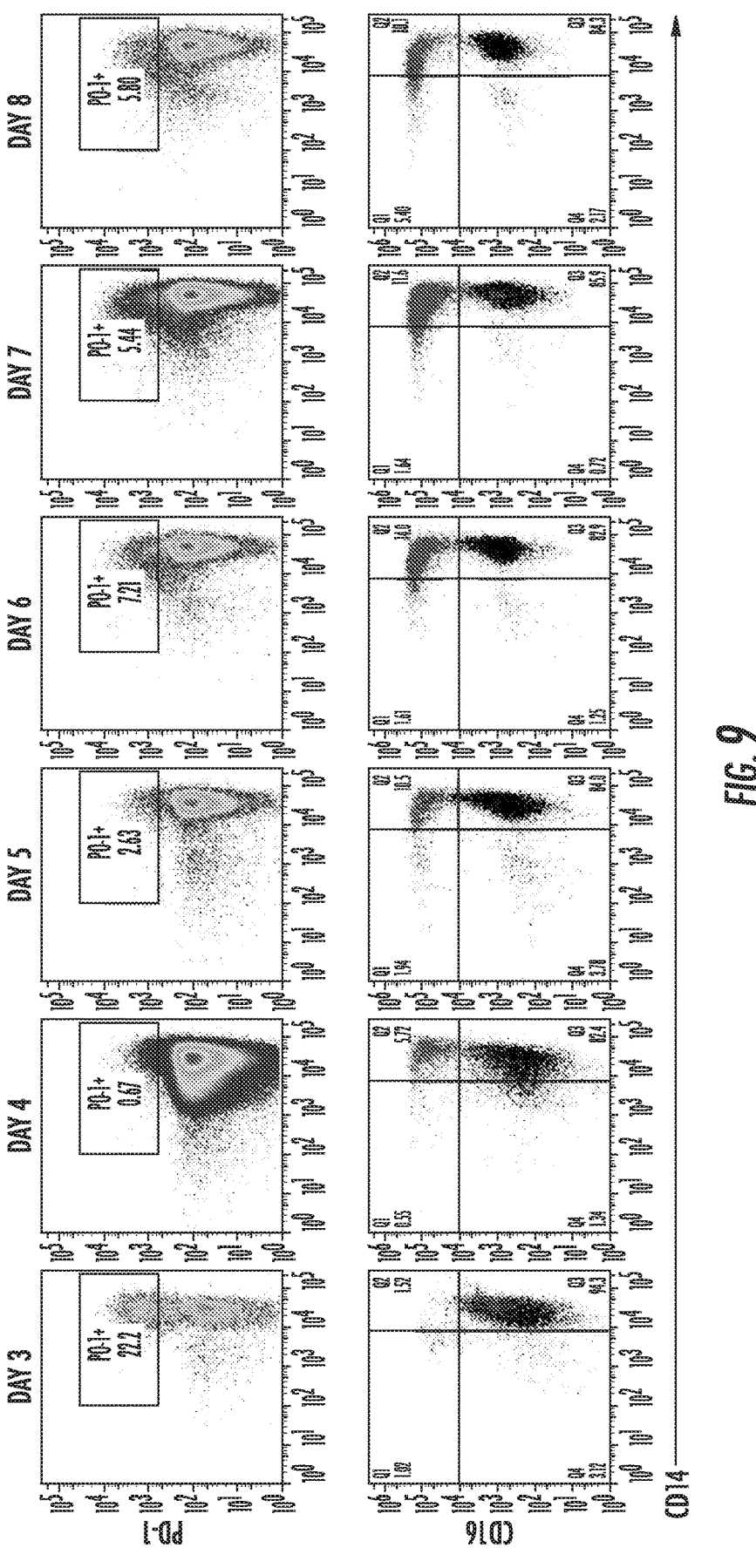
FIG. 9. Representative flow cytometry plots for Patient 1 days 3-8 after aneurysm rupture. In the CD 14 vs. CD16 plots red dots represent PD-1+ cells.

To determine if PD-1+ monocyte frequency in the periph-eral blood correlates with cerebral vasospasm the present inventors studied six consecutive patients admitted to the present inventors' institution with aSAH. Patient and aneu-rysm characteristics are summarized in Table 1. The per-centage of monocytes in the peripheral blood expressing PD-1 was serially measured for up to 14 days after aneurysm rupture as shown in FIG. 8. In the two patients who developed radiographically confirmed vasospasm in the hospital (Patients 1 and 5), vasospasm was preceded by an increase in PD-1+ monocyte frequency in the peripheral blood. Patient 5 exhibited an elevated frequency of circu-lating PD-1+ monocytes beginning on day 6, which peaked on day 7 at 9.31% (FIG. 3A). On day 8, Patient 5 developed blood pressure-dependent aphasia and computed tomogra-phy angiography (CTA) confirmed vasospasm in the left middle cerebral artery. Transcranial doppler ultrasound (TCD) also detected elevated cerebral blood flow velocities on day 7 (FIG. 3B). Patient 1 presented to the hospital on the third day after aneurysm rupture. Twenty-two percent of Patient 1's peripheral blood monocytes were PD-1+ at presentation (FIG. 9). On day 4, there was an increase in TCD velocities that continued to rise until day 8 (FIG. 3B). Radiographic vasospasm was demonstrated by magnetic resonance angiography (MRA) on day 5 and confirmed by catheter-based cerebral angiography on day 10.

TABLE 1

| | | | | | Hunt | | | Clinical and/or |
| Patient | Gender | Age | Aneurysm Location | Admission GCS | and Hess | Modified Fisher | Aneurysm Treatment | radiographic vasospasm |
|---|---|---|---|---|---|---|---|---|
| 1 | Female | 57 | Superior cerebellar artery | 7 | 4 | 4 | Coiled | Yes |
| 2 | Female | 58 | Posterior communicating artery | 14 | 2 | 4 | Coiled | No |
| 3 | Female | 83 | Posterior communicating artery | 6 | 5 | 4 | Coiled | No |
| 4 | Female | 66 | Basilar artery | 15 | 2 | 3 | Coiled | Yes |
| 5 | Female | 54 | Posterior communicating artery | 15 | 2 | 3 | Clipped | Yes |
| 6 | Female | 51 | Middle cerebral artery | 7 | 4 | 3 | Clipped | No |

Patient and aneurysm characteristics

11

In both patients there was an early abundance of CD14++, CD16– (classical) monocytes followed by an increase in the CD14++, CD16+ (intermediate) population and a slower increase in the CD14+, CD16+ (non-classical) population (FIG. 3A, FIG. 9). This pattern has been described as a negative prognostic indicator in other vascular pathologies, including acute myocardial infarction and ischemic stroke.[26] PD-1+ monocytes were generally of the CD14++, CD16+ (intermediate) subtype (FIG. 3A), which has been linked to cardiovascular events in patients with chronic kidney disease as well as disease severity in rheumatoid arthritis.[26] The finding that PD-1 is expressed on intermediate monocytes suggests that PD-1 may be a more general marker of inflammatory monocytes and a potential target for intervention in a variety of inflammatory disease processes.

Figure 3E:
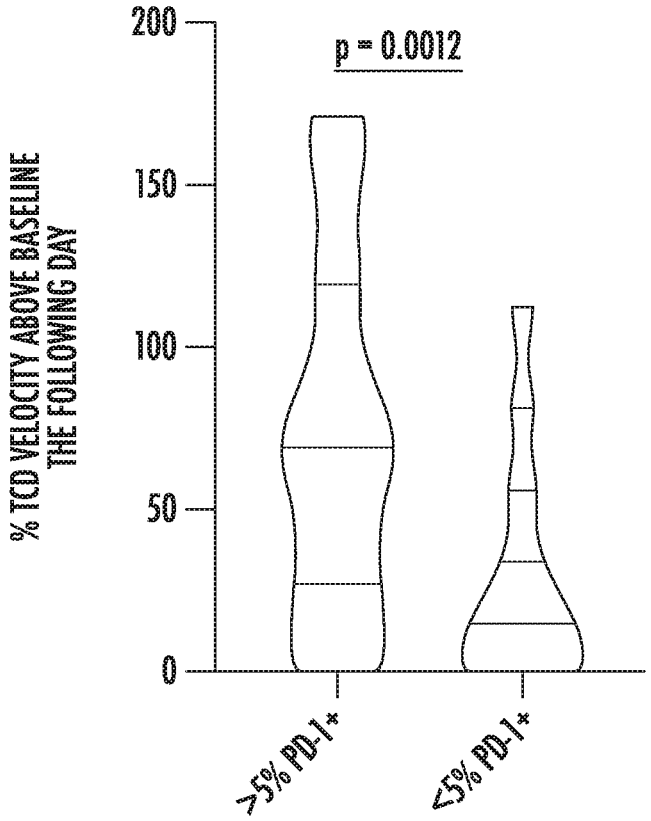
Figure 10:
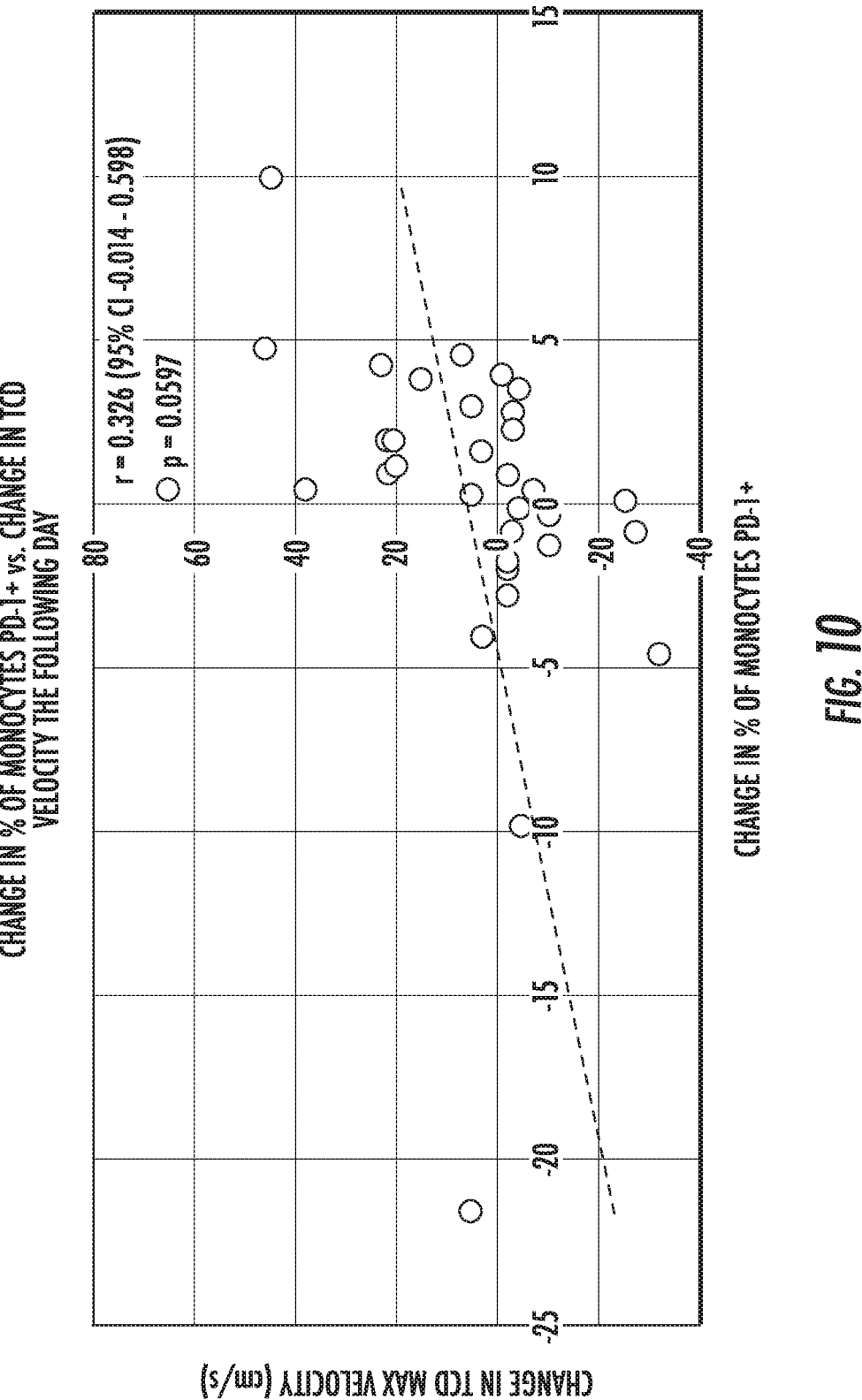
FIG. 10. Change in % of monocytes PD-1+ vs. change in maximum TCD velocity the following day including the Patient 1, day 3 datapoint. Correlation coefficient (r)=0.326 (95% CI −0.14-0.598, p=0.0597).

Based on the present inventors' preclinical data indicating that PD-1+ monocytes originate from the bone marrow the present inventors hypothesized that vasospasm might be preceded by an increase in PD-1+ monocyte frequency in the peripheral blood. The present inventors paired daily changes in PD-1+ monocyte frequency with daily changes in maximum TCD velocities the following day. An inter-rater agreement between the daily change of PD-1+ monocyte frequency and changes in maximum TCD velocities the following day was assessed by Cohen's kappa coefficient, ($\kappa$=0.48 (95% CI: 0.2-0.76; p=0.0018) (FIG. 3C). Dichotomizing PD-1+ monocytes into high a low frequency showed that >5% PD-1+ monocytes was associated with higher TCD velocities the following day compared with <5% PD-1+ monocytes (p=0.0012) (FIG. 3D). Finally, a possible correlation was estimated using Pearson correlation coefficient at r=0.33 (95% CI:–0.01-0.60; p=0.06) with all data pairs (FIG. 10). It is plausible that the rise in TCD velocities observed on days 4-8 reflects a dramatic increase in PD-1+ monocyte frequency on days 1-2, which was not captured due to the patient's delayed presentation. Therefore, the present inventors performed a sensitivity analysis excluding the day 3 outlier and found r=0.486 (95% CI: 0.17-0.71; p=0.0037) (FIG. 3E). The present inventors anticipate that confirmative studies in larger patient cohorts will refine the parameters of this assay as a clinical biomarker of cerebral vasospasm.

Figure 4A:
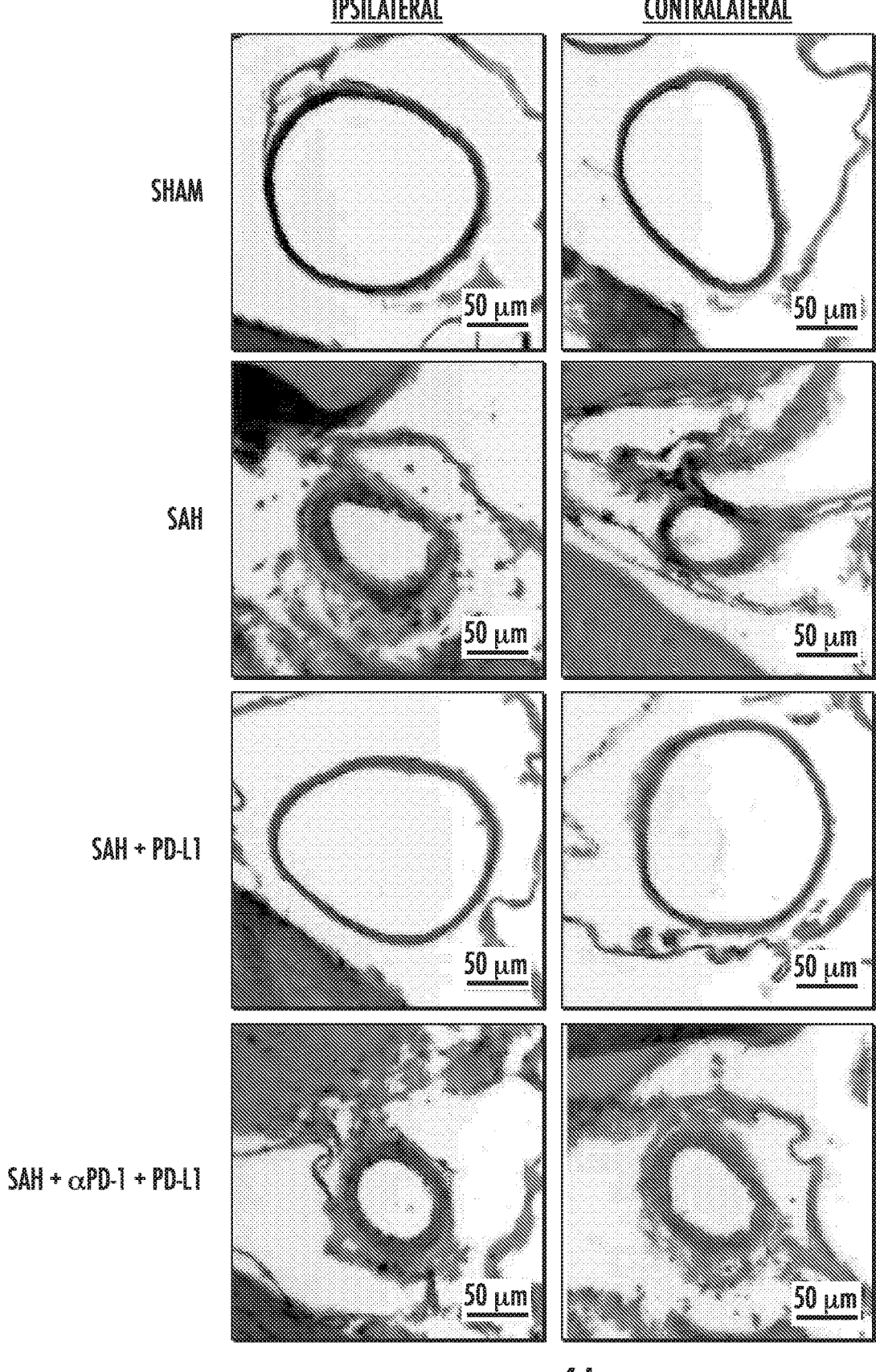
FIG. 4A-4G. Administration of PD-L1 prevents cerebral vasospasm by inhibiting migration of activated monocytes into the CNS.
Figure 4B:
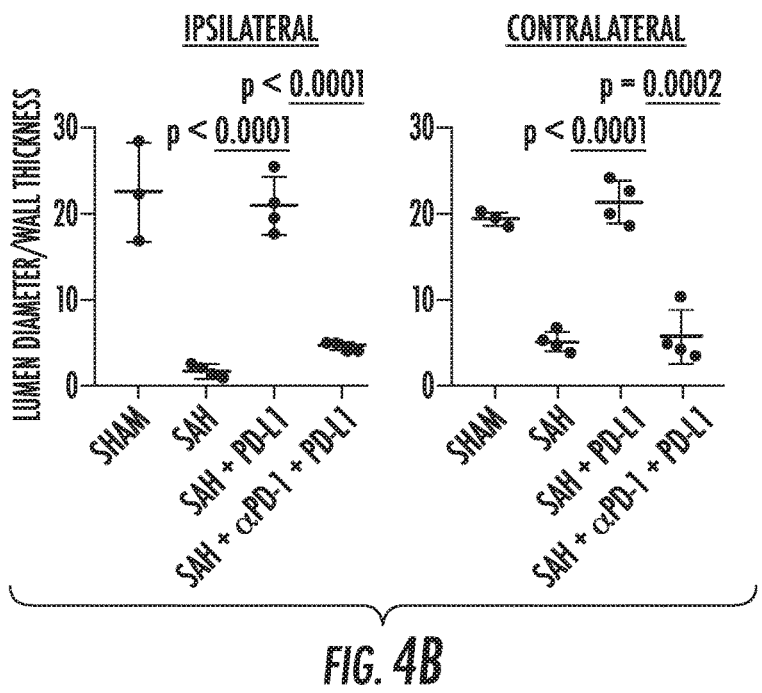
Figure 4C:
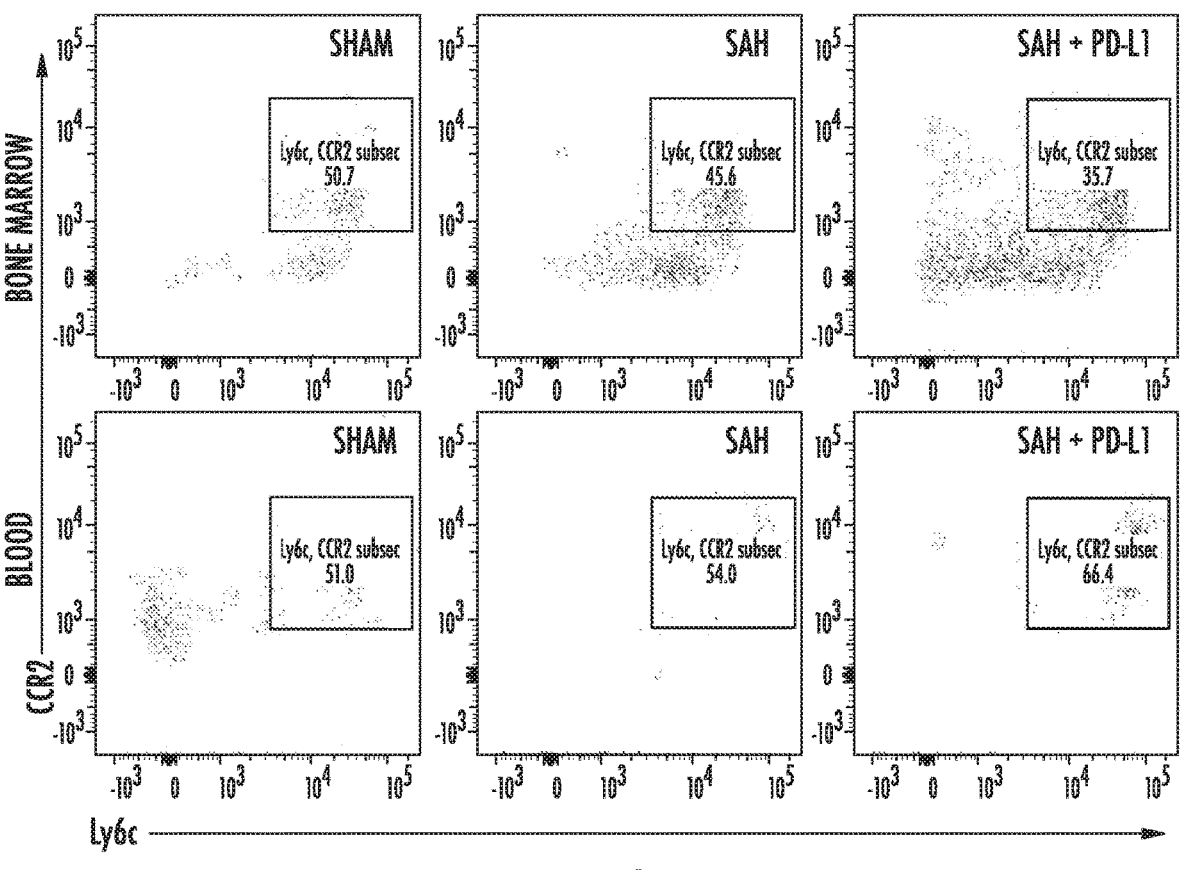
Figures 4D, 4E:
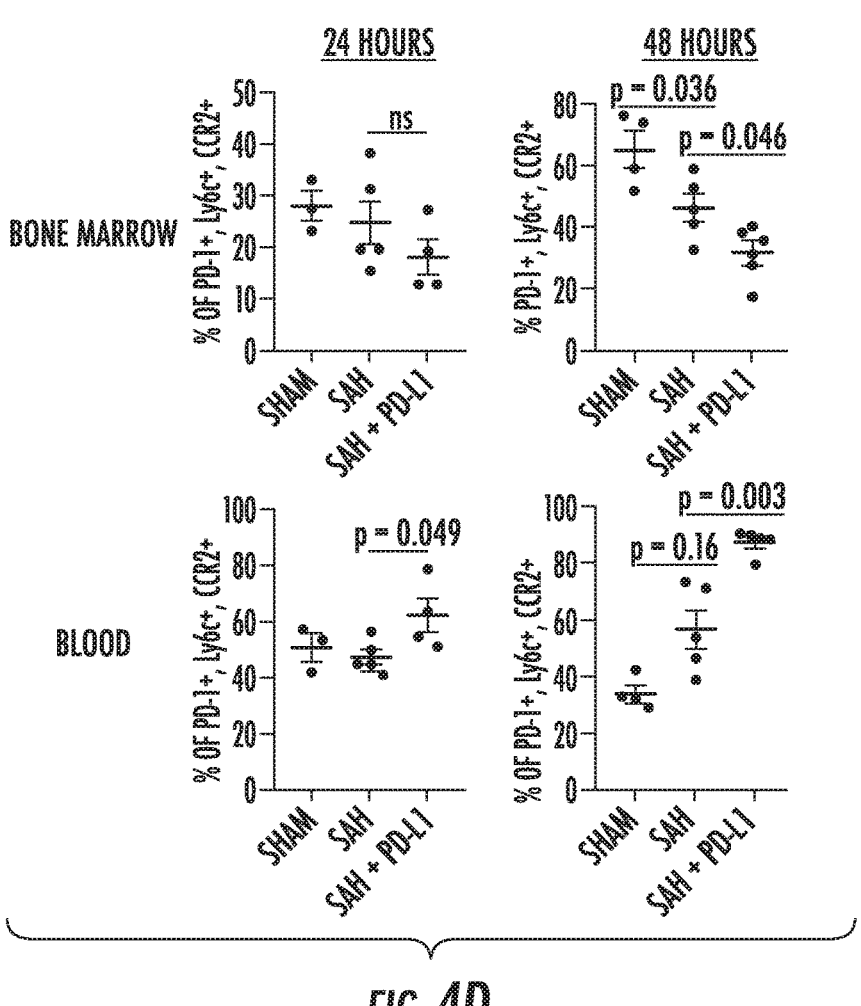
Figure 4F:
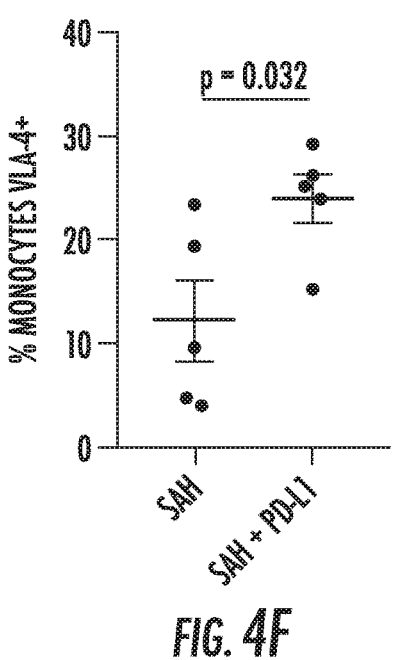
Figure 4G:
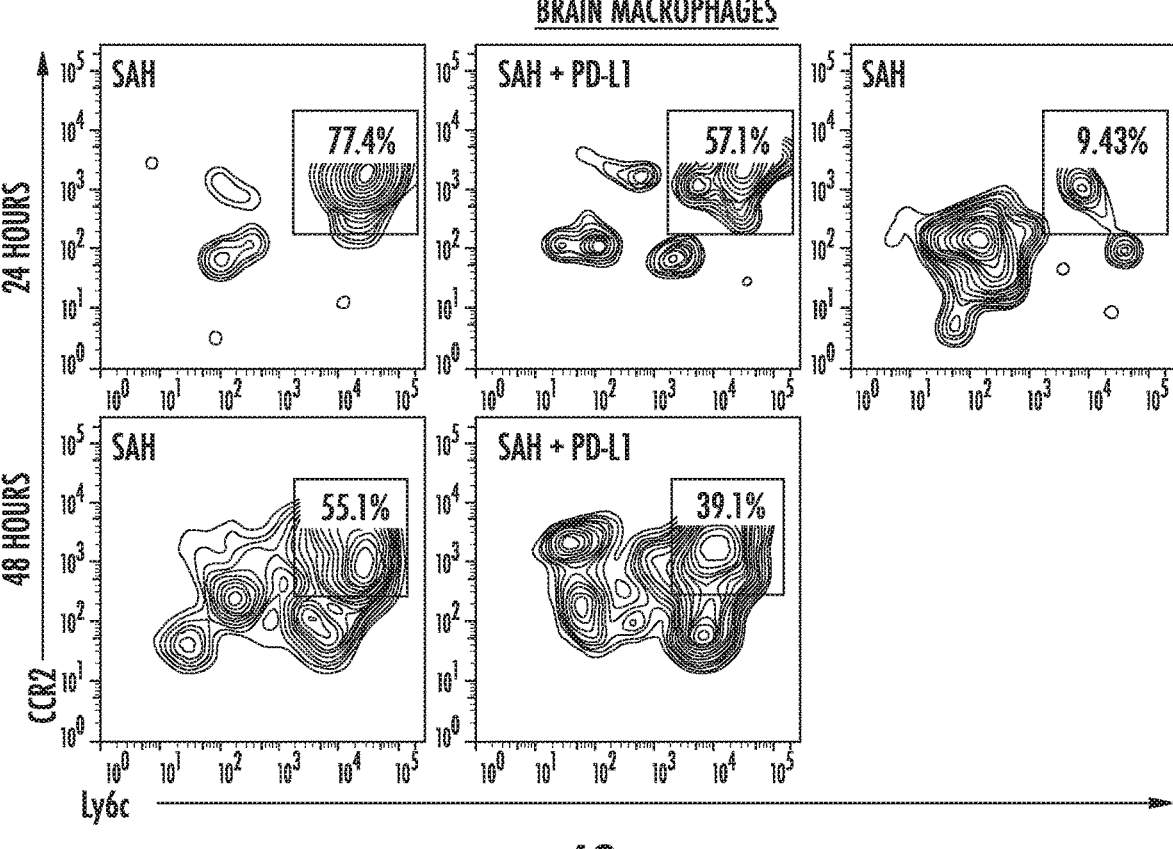

To evaluate PD-1 as a therapeutic target for cerebral vasospasm the present inventors administered PD-L1 via IP injection 1 hour after SAH and measured the terminal ICA at 48 hours (FIG. 4A). The present inventors found that administration of PD-L1 prevented vasospasm while pretreatment with PD-1 blocking antibodies 1 hour prior to SAH abrogated the therapeutic effect of PD-L1 (FIG. 4B). Ly6c+ monocytes are activated in the bone marrow and licensed to migrate into tissue and exert inflammatory functions.[27] CC chemokine receptor 2 (CCR2)-expressing monocytes have been implicated in inflammatory central nervous system (CNS) pathologies.[28] When the present inventors measured Ly6c and CCR2 expression on PD-1+ monocytes in the blood, bone marrow, and brain at 24 hours and 48 after SAH the present inventors found a higher frequency of PD-1+ monocytes in the blood of PD-L1 treated mice compared with untreated animals (FIG. 4C, 4D). In addition, PD-L1-treated animals had a higher frequency of blood monocytes expressing very late antigen-4 (VLA-4) (FIG. 4E, 4F), an adhesion molecule that facilitates transmigration across vascular endothelium[29] and has been identified as a mediator of CNS inflammation[30]. Analysis of brain-infiltrating monocytes at these timepoints showed a correspondingly lower frequency of Ly6c+, CCR2+ monocytes in PD-L1 treated animals (FIG. 4G). While caution is warranted as CCR2 is downregulated by monocytes upon entry into tissue[28], these data nevertheless indicate that PD-1 signaling in the setting of SAH prevents vasospasm by inhibiting ingress of activated monocytes into the CNS.

Aberrant inflammation is observed in patients with cerebral vasospasm; however, the details of this immune response have been elusive. The present inventors' results show that activated, PD-1+ monocytes are released from the bone marrow following SAH in a catecholamine-dependent fashion. Systemic of PD-L1 prevents cerebral vasospasm by inhibiting migration of inflammatory monocytes into the CNS. This work identifies a novel role for PD-1 in monocyte migration and suggests that PD-1 agonists may be effective in preventing cerebral vasospasm in patients with aSAH.

REFERENCES

1. Ferro, J. M., Canhao, P. & Peralta, R. Update on subarachnoid haemorrhage. *J Neurol* 255, 465-479 (2008).
2. Charpentier, C., Audibert, G., Guillemin, F., Stroke, T. C. 1999. Multivariate analysis of predictors of cerebral vasospasm occurrence after aneurysmal subarachnoid hemorrhage. *Am Heart Assoc*
3. Hijdra, A., Van Gijn, J., Nagelkerke, N. J., Stroke, M. V. 1988. Prediction of delayed cerebral ischemia, rebleeding, and outcome after aneurysmal subarachnoid hemorrhage. *Am Heart Assoc*
4. Chaichana, K. L., Levy, A. P., Miller-Lotan, R., Shakur, S. & Tamargo, R. J. Haptoglobin 2-2 Genotype Determines Chronic Vasospasm After Experimental Subarachnoid Hemorrhage. *Stroke* 38, 3266-3271 (2007).
5. Barber, D. L. et al. Restoring function in exhausted CD8 T cells during chronic viral infection. *Nature* 439, 682-687 (2005).
6. Fife, B. T. & Pauken, K. E. The role of the PD-1 pathway in autoimmunity and peripheral tolerance. *Annals of the New York Academy of Sciences* 1217, 45-59 (2011).
7. Dong, H. et al. Tumor-associated B7-H1 promotes T-cell apoptosis: A potential mechanism of immune evasion. *Nat Med* 8, 793-800 (2002).
8. Topalian, S. L., Drake, C. G. & Pardoll, D. M. Immune Checkpoint Blockade: A Common Denominator Approach to Cancer Therapy. *Cancer Cell* 27, 450-461 (2015).
9. Gaetani, P., Tartara, F., Pignattit, P., Neurological, F. T. 1998. Cisternal CSF levels of cytokines after subarachnoid hemorrhage. *Taylor & Francis* 20, 337-342 (2016).
10. Kaynar, M. Y. et al. Detection of soluble intercellular adhesion molecule-1 and vascular cell adhesion molecule-1 in both cerebrospinal fluid and serum of patients after aneurysmal subarachnoid hemorrhage. *Journal of Neurosurgery* 101, 1030-1036 (2019).
11. Polin, R. S. et al. Detection of soluble E-selectin, ICAM-1, VCAM-1, and L-selectin in the cerebrospinal fluid of patients after subarachnoid hemorrhage. *Journal of Neurosurgery* 89, 559-567 (2019).
12. Kikuchi, T., Okuda, Y., Kaito, N., research, T. A. N. 1995. Cytokine production in cerebrospinal fluid after subarachnoid haemorrhage. *Taylor & Francis* 17, 106-108 (2016).
13. Xie, X., Wu, X., Cui, J., Li, H. & Yan, X. Increase ICAM-1 and LFA-1 expression by cerebrospinal fluid of subarachnoid hemorrhage patients: Involvement of TNF-α. *Brain Research* 1512, 89-96 (2013).
14. Schneider, U. C., Schiffler, J., Hakiy, N., Horn, P. & Vajkoczy, P. Functional analysis of Pro-inflammatory properties within the cerebrospinal fluid after subarachnoid hemorrhage in vivo and in vitro. *J Neuroinflammation* 9, 330-2 (2012).

15. Barrow, J., Turan, N., Wangmo, P., Roy, A. & Pradilla, G. The role of inflammation and potential use of sex steroids in intracranial aneurysms and subarachnoid hemorrhage. *Surg Neurol Int* 9, 150-2 (2018).

16. Froehler, M. T. et al. Vasospasm after subarachnoid hemorrhage in haptoglobin 2-2 mice can be prevented with a glutathione peroxidase mimetic. *Journal of Clinical Neuroscience* 17, 1169-1172 (2010).

17. Schallner, N. et al. Microglia regulate blood clearance in subarachnoid hemorrhage by heme oxygenase-1. *J. Clin. Invest.* 125, 2609-2625 (2015).

18. Kubota, T., Handa, Y., Tsuchida, A., Stroke, M. K. 1993. The kinetics of lymphocyte subsets and macrophages in subarachnoid space after subarachnoid hemorrhage in rats. *Am Heart Assoc* 24, 1993-2000 (1993).

19. Provencio, J. J. et al. CSF Neutrophils Are Implicated in the Development of Vasospasm in Subarachnoid Hemorrhage. *Neurocrit Care* 12, 244-251 (2009).

20. Spitzer, D. et al. Activation of Cytotoxic Natural Killer Cells After Aneurysmal Subarachnoid Hemorrhage. *World Neurosurgery* 101, 666-676.e1 (2017).

21. Huang, X. et al. PD-1 expression by macrophages plays a pathologic role in altering microbial clearance and the innate inflammatory response to sepsis. *Proceedings of the National Academy of Sciences* 106, 6303-6308 (2009).

22. Loftus, T. J., Efron, P. A., Moldawer, L. L. & Mohr, A. M. β-Blockade use for Traumatic Injuries and Immunomodulation. *SHOCK* 46, 341-351 (2016).

23. Bunc, G., Kovacic, S. & Strnad, S. The influence of noradrenergic blockade on vasospasm and the quantity of cerebral dopamine ε-hydroxylase following subarachnoid haemorrhage in rabbits. *Wien Klin Wochenschr* 115, 652-659 (2003).

24. Chalouhi, N. et al. Beta-blocker therapy and impact on outcome after aneurysmal subarachnoid hemorrhage: a cohort study. *Journal of Neurosurgery* 125, 730-736 (2019).

25. Chang, M. M. et al. Beta Blockade and Clinical Outcomes in Aneurysmal Subarachnoid Hemorrhage. *TONEUJ* 10, 155-163 (2016).

26. Stansfield, B. K. & Ingram, D. A. Clinical significance of monocyte heterogeneity. *Clin Trans Med* 4, 2527-2 (2015).

27. Mildner, A. et al. Genomic Characterization of Murine Monocytes Reveals C/EBPO Transcription Factor Dependence of Ly6C—Cells. *Immunity* 46, 849-862.e7 (2017).

28. Prinz, M. & Priller, J. Tickets to the brain: Role of CCR2 and CX3CR1 in myeloid cell entry in the CNS. *Journal of Neuroimmunology* 224, 80-84 (2010).

29. Huo, Y., Hafezi-Moghadam, A., research, K. L. C. 2000. Role of vascular cell adhesion molecule-1 and fibronectin connecting segment-1 in monocyte rolling and adhesion on early atherosclerotic lesions. *Am Heart Assoc.*

30. Yednock, T. A. et al. Prevention of experimental autoimmune encephalomyelitis by antibodies against α4β1 integrin. *Nature* 356, 63-66 (1992).

Example 2: PD-1 Expression on Monocytes as a Biomarker of Pathologic Central nervous system inflammation. Using a mouse model of intracranial hemorrhage and vasospasm (endovascular perforation), the present inventors have shown that administration of soluble PD-L1 reduces perivascular inflammation and prevents cerebral vasospasm. This effect is abrogated by pretreatment with PD-1 blocking antibodies, which are commonly used in cancer immunotherapy, validating that PD-1, which is the only known ligand of PD-L1, is the mediator of this effect (FIG. 4A-4B).

Figure 11:
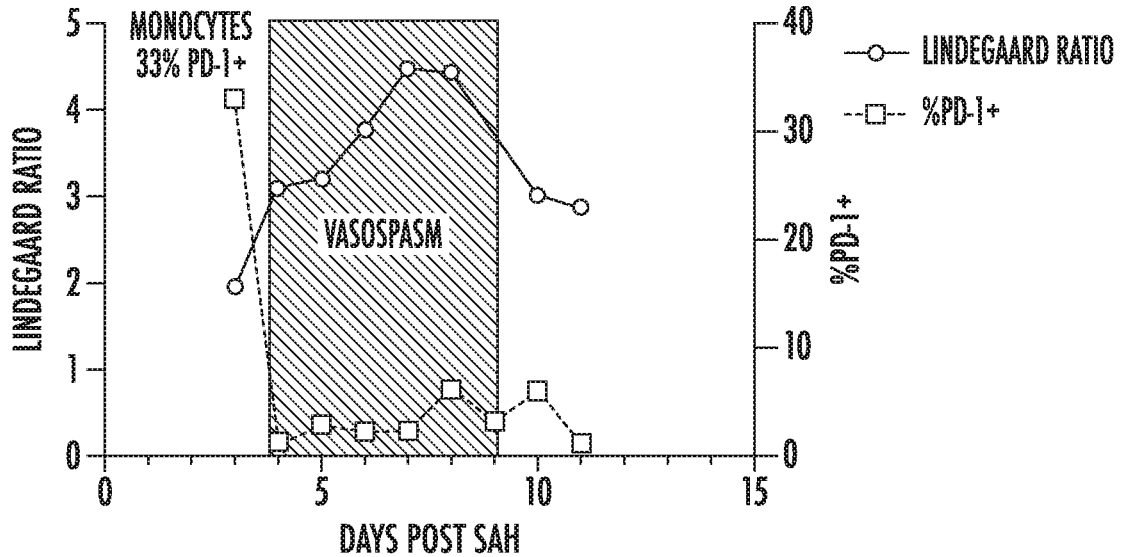
FIG. 11. A 57 year-old female who presented with headache for 3 days and mental status changes was found to have subarachnoid hemorrhage form a ruptured intracranial aneurysm. Peripheral blood was analyzed daily for PD-1 expression on monocytes using the protocol below. A spike in PD-1+ monocytes was observed the day prior to vasospasm as determined by transcranial doppler ultrasound and vascular imaging. During vasospasm PD-1 levels remained

The present inventors have discovered that PD-1 expression on CD45+, CD11 b+, CDIIb+, CD3–, CD15–, CD19– cells (monocytes) in the peripheral blood is elevated in patients with aneurysmal subarachnoid hemorrhage (aSAH) compared with normal controls. Importantly, cerebral vasospasm is preceded by a roughly 10-fold increase in the percent of monocytes expressing PD-1 (FIG. 11). The present inventors envision this discovery being translated clinically as a biomarker of pathologic brain inflammation in aneurysmal subarachnoid hemorrhage, hemorrhagic and ischemic stroke, as well as traumatic brain injury.

Patients with these conditions would have blood drawn daily and PD-1 expression would be measured on monocytes by flow cytometry as described below. Based on the present inventors' data, the present inventors expect that an increase in PD-1 expression on monocytes 3-fold or more above baseline (this threshold will be refined as more patient data are collected) indicates impending brain inflammation and the associated sequelae thereof (vasospasm, stroke, neuronal damage, cognitive decline, etc).

Given the present inventors' discovery that soluble PD-L1 prevents the sequelae of monocyte-mediated cerebral inflammation in mice, the present inventors believe that this test will be valuable as a companion diagnostic to PD-L1, its analogues, or other PD-1 agonists. The proposed algorithm would be to administer the PD-1 agonist to patients with elevated PD-1 monocytes. Mechanistically, this will disable the inflammatory monocytes in the blood prior to ingress into the brain. Dosing of full-length, unmodified PD-L1 in mice suggests a daily dosing schedule is effective. The duration of treatment is yet to be determined, but the present inventors' data show that PD-1 remains elevated on monocytes for at least one week from the initial spike in this cell population and correlates with elevated blood flow velocities measured by transcranial doppler ultrasound, which is currently the standard method for vasospasm monitoring.

Flow Cytometry Protocol for Quantifying PD-1+ Monocytes. Consent for blood collection was obtained for all patients as indicated in the approved protocol from the Institutional Review Board (IRB).

Specimen collection and processing for peripheral blood mononuclear cells (PBMC). Five cc whole blood were collected in ethylenediaminetetraacetic acid (EDTA) tubes, which were subsequently mixed with an equal volume of phosphate buffered saline (PBS). Twelve ml of room temperature Ficoll-Paque™ Plus (density gradient media) was underlaid via pasteur pipette with the graded solution centrifuged at 2200 rpm for 20 minutes without breaks at room temperature in a Sorvall Legend XIR centrifuge. The buffy coat was then extracted and mixed into a 40 ml solution of PBS before being spun at 1400 rpm for 5 minutes at room temperature. The supernatant was decanted and samples were resuspended in 30 ml PBS before being centrifuged at 1000 rpm for 10 minutes to remove platelets. Cell pellets were resuspended in 1 ml PBS and counted using a hemocytometer.

PD-1+ myeloidpanel staining. Cells were stained for several extracellular markers in specific dilutions with PBS as shown in Table 2. FcBlock was used to prevent nonspecific Fc receptor binding of flow antibodies to myeloid cells. Samples were stained with fluorophore conjugated antibodies for 30 minutes in 4° C. with minimal light exposure. Samples were washed with PBS twice before and after staining.

TABLE 2

| Marker | Fluorophore | Dilution (in PBS) |
|---|---|---|
| CD45 | AF700 | 1:100 |
| CD11b | BV421 | 1:100 |
| CD14 | APC-Cy7 | 1:50 |
| CD16 | PE-Cy7 | 1:50 |
| PD-1 | PE | 1:100 |
| CD3 | FITC | 1:20 |
| CD15 | FITC | 1:200 |
| CD19 | FITC | 1:100 |

Flow cytometry gating strategy. Cells were gated to maximize signal readout from CD14+ monocytes for PD-1 (see FIG. 11). A lineage "dump gate" was used to exclude other cell types that were not of interest (i.e. neutrophils, B lymphocytes, T lymphocytes). Fluorescence minus one (FMO) samples were used to replace isotype controls for PD-1+ staining. FMOs were used each day to compare relative PD-1 monocyte expression of samples.

Example 3: a Common Pattern of Monocyte-Mediated Pathologic Inflammation Links Brain Injury/Vasospasm and Other CNS as Well as Some Non-CNS Inflammatory Diseases Since PD-1 has not been identified previously as a marker and potential target for treating the pathologic inflammation underlying these disease processes, the present inventors' findings in SAH may have broader applicability as PD-L1 may have activity in any disease process mediated by these inflammatory monocytes. Analysis of this novel PD-1+ monocyte population initially identified in the present inventors' mouse model and subsequently identified in aSAH patients shows that this pathogenic, PD-1+ cell population undergoes a transition from a CD14+, CD16– classical phenotype to CD14+, CD16+ intermediate phenotype in the days following brain injury. This pattern correlates with the pattern reported in other disease processes. For example, in myocardial infarction the peak of CD14+, CD16– classical monocytes is a negative prognostic indicator for myocardial salvage (FIG. 12). Analogously, the present inventors found that vasospasm in aSAH is preceded by a high level of CD14+, CD16– monocytes (FIG. 12). Combining the present inventors' finding that these monocytes express PD-1 in patients with the present inventors' murine data showing that PD-L1 administration mitigates the pathologic sequelae of this cell population, it is reasonable to hypothesize that PD-L1 or its analogues may be a treatment for preventing cardiac ischemic damage or other inflammatory diseases associated with this pattern of monocyte activation.

The present inventors' data show that PD-1+ monocytes persist at low levels in the blood during the vasospasm period. These cells transition from CD14+, CD 16– to CD14+, CD16+ monocytes. CD14+, CD16+ monocytes are "intermediate" monocytes, which have been implicated in several autoimmune and chronic inflammatory disorders, including cardiovascular disease, Crohn's disease, kidney disease, and rheumatoid arthritis. However, PD-1 as a disease-modifying target has never been described in these conditions. Based on the present inventors' discovery of PD-1 on this known pathogenic cell population it is plausible that PD-L1 is likely to have disease-modifying activity in treating these conditions.

Summary Treatment with PD-L1 prevents the inflammatory sequela of vasospasm by acting as a PD-1 agonist in a mouse model of subarachnoid hemorrhage. Analysis of aSAH patient blood monocytes shows that a dramatic increase in PD-1 expression precedes vasospasm as these pathogenic cells traverse the blood en route to the brain. Therefore, the present inventors propose that PD-1+ monocytes are a biomarker of impending vasospasm and have developed a flow cytometry-based assay for measuring PD-1 expression on this cell population. Given the present inventors' discovery that PD-L1 administration prevents cerebral inflammation and prevents vasospasm in mice, the present inventors additionally posit that measuring PD-1 using this method can be used as a companion diagnostic to PD-L1 or any other PD-1 agonist developed for this purpose. Furthermore, the present inventors have discovered that this PD-1+ monocyte population follows a pattern of CD14/CD16 expression after brain injury that mirrors the pattern described in other inflammatory pathologies. However, the present inventors are the first to identify PD-1 on this cell population and demonstrate that PD-1 signaling prevents the pathologic inflammation caused by these monocytes. Accordingly, via investigation into the mechanisms by which PD-L1 mitigates brain inflammation and prevents vasospasm, the present inventors have discovered a novel target for treatment of diseases mediated by inflammatory monocytes expressing PD-1.

That which is claimed:

1. A method comprising:
  a. measuring programmed death-1 (PD-1) expression on monocytes in a blood sample obtained from a patient, wherein the patient has suffered a hemorrhagic or ischemic stroke; and
  b. treating the patient with soluble PD-L1 if the PD-1 expression is increased relative to a control.

2. The method of claim 1, wherein the PD-1 expression on monocytes is measured using flow cytometry.

3. The method of claim 1, wherein the soluble PD-L1 is a PD-L1 fusion protein.

4. The method of claim 1, wherein the patient suffers from an aneurysmal subarachnoid hemorrhage.

5. The method of claim 1, wherein the patient has cerebral vasospasm.

6. The method of claim 1, wherein the patient has suffered a brain injury.

7. A method comprising administering to a patient having an increased PD-1 expression on monocytes relative to a control soluble PD-L1, wherein the patient has suffered a hemorrhagic or ischemic stroke.

8. The method of claim 7, wherein the soluble PD-L1 is a PD-L1 fusion protein.

9. The method of claim 7, wherein the patient suffers from an aneurysmal subarachnoid hemorrhage.

10. The method of claim 7, wherein the patient has cerebral vasospasm.

11. The method of claim 7, wherein the patient has suffered a brain injury.

12. The method of claim 7, wherein the patient has or is suspected of having a monocyte-cerebral inflammation.

13. A method for treating cerebral vasospasm in a patient comprising the step of administering to the patient soluble PD-1, wherein a blood sample obtained from the patient comprises elevated PD-1 expression on monocytes relative to a control.

14. The method of claim 13, wherein the patient has suffered a brain injury.

15. The method of claim 13, wherein the patient has suffered a stroke.

16. The method of claim 13, wherein the patient has suffered a myocardial infarction.

* * * * *